(12) United States Patent
Subbaraju et al.

(10) Patent No.: US 8,524,782 B2
(45) Date of Patent: Sep. 3, 2013

(54) KEY INTERMEDIATE FOR THE PREPARATION OF STILBENES, SOLID FORMS OF PTEROSTILBENE, AND METHODS FOR MAKING THE SAME

(75) Inventors: Gottumukkala V. Subbaraju, Tirupati (IN); Masna Mahesh, Hyderabad (IN); Hindupur R. Mohan, Hyderabad (IN); Thatipally Suresh, Hyderabad (IN); Igor Ivanisevic, West Lafayette, IN (US); Mark Andres, West Lafayette, IN (US); Kyle Stephens, Farmland, IN (US)

(73) Assignee: Laurus Labs Private Limited (IN)

( * ) Notice: Subject to any disclaimer, the term of this patent is extended or adjusted under 35 U.S.C. 154(b) by 245 days.

(21) Appl. No.: 13/011,593

(22) Filed: Jan. 21, 2011

(65) Prior Publication Data

US 2011/0144212 A1    Jun. 16, 2011

Related U.S. Application Data

(63) Continuation-in-part of application No. PCT/IN2009/000313, filed on Jun. 1, 2009, and a continuation-in-part of application No. PCT/US2010/022285, filed on Jan. 27, 2010.

(30) Foreign Application Priority Data

Jul. 23, 2008  (IN) .......................... 1766/CHE/2008
Mar. 22, 2010  (IN) ............................ 741/CHE/2010

(51) Int. Cl.
*A01N 31/14*   (2006.01)
*A61K 31/075*  (2006.01)

(52) U.S. Cl.
USPC ............ 514/720; 568/646; 568/729; 549/416

(58) Field of Classification Search
None
See application file for complete search history.

(56) References Cited

U.S. PATENT DOCUMENTS 7,253,324 B1    8/2007  Majeed et al.

FOREIGN PATENT DOCUMENTS

CN    1948274 A    4/2007
CN    1955153 A    5/2007

OTHER PUBLICATIONS

Author Unknown, "Pterostilbene Chemical Properties, Usage, Production," Chemical Book, 2007, 2 pp., retrieved from the Internet at http://www.chemicalbook.com/chemicalproductproperty_en_cb1373369.htm.
Shen, et al., "A Practical Synthesis of Trans-Resveratrol", Indian Journal of Chemistry, 2002, pp. 2395-2398, vol. 41B.
Li, et al., "Synthesis of Stilbene Derivatives with Inhibition of SARS Coronavirus Replication", European Journal of Medicinal Chemistry, 2006, pp. 1084-1089, vol. 41.
Mallavadhani, et al., "Pterostilbene: A Highly Reliable Quality-Control Marker for the Ayurvedic Antidiabetic Plant 'Bijasar'", Chromatographia, 2003, pp. 307-312, vol. 58.
Breuil, et al., "Characterization of a Pterostilbene Dehydrodimer Produced by Laccase of *Botrytis cinerea*", Biochemistry and Cell Biology, 1999, pp. 298-302, vol. 89, No. 4.
Pezet, et al., "Purification and Characterization of a 32-kDa Laccase-Like Stilbene Oxidase Produced by *Botrytis cinerea* Pers.:FR.", 1998, pp. 203-208, vol. 167.
Lopez-Nicolas, et al., "Physicochemical Study of the Complexation of Pterostilbene by Natural and Modified Cyclodextrins", Journal of Agricultural and Food Chemistry, 2009, pp. 5294-5300, vol. 57.
Pettit, et al., "Antineoplastic Agents. 465. Structural Modification of Resveratrol: Sodium Resverastatin Phosphate", Journal of Medical Chemistry, 2002, pp. 2534-2542, vol. 45.

*Primary Examiner* — Brandon Fetterolf
*Assistant Examiner* — Jean Cornet
(74) *Attorney, Agent, or Firm* — Blank Rome LLP

(57) ABSTRACT

The present invention provides a scalable process for the preparation of stilbenes by (i) condensing 3,5-dialkylbenzyl phosphonates with 4'-O-tetrahydropyranyl benzaldehyde to get 3,5-alkyl-4'-O-tetrahydropyranyl Stilbene and (ii) deprotecting the obtained 3,5-Dialkyl-4'-O-tetrahydropyranylstilbene to yield stilbenes. The present invention also provides a novel intermediate 3,5-Dialkyl-4'-O-tetrahydropyranyl stilbene, which is a key intermediate for the synthesis of stilbenes such as Pterostilbene and Resveratrol. The present invention also provides characteristics of various solid forms of Pterostilbene, methods for their preparation, as well as dosage forms containing the same for administration to or consumption by humans.

39 Claims, 20 Drawing Sheets

Experimental XRPD Spectra Stackplot of Solid Forms of Pterostilbene

RAMAN PEAK LIST

| FORM I PEAKS | FORM II PEAKS | FORM III PEAKS | FORM IV PEAKS | FORM V PEAKS |
|---|---|---|---|---|
| 134 | 113 | 151 | 134 | 159 |
| 159 | 162 | 179 | 161 | 193 |
| 195 | 183 | 193 | 200 | 228 |
| 270 | 201 | 232 | 268 | 252 |
| 383 | 261 | 273 | 318 | 274 |
| 400 | 278 | 324 | 379 | 381 |
| 410 | 317 | 378 | 395 | 397 |
| 430 | 377 | 396 | 411 | 452 |
| 451 | 395 | 419 | 455 | 493 |
| 502 | 411 | 428 | 497 | 513 |
| 509 | 455 | 451 | 518 | 524 |
| 517 | 496 | 492 | 542 | 594 |
| 541 | 519 | 511 | 600 | 608 |
| 600 | 591 | 526 | 611 | 644 |
| 644 | 611 | 547 | 644 | 685 |
| 667 | 645 | 594 | 669 | 719 |
| 719 | 672 | 608 | 686 | 803 |
| 805 | 686 | 613 | 718 | 829 |
| 865 | 719 | 644 | 804 | 840 |
| 925 | 800 | 687 | 827 | 867 |
| 941 | 808 | 718 | 845 | 922 |
| 967 | 813 | 801 | 862 | 936 |
| 976 | 828 | 814 | 924 | 962 |
| 991 | 844 | 840 | 961 | 994 |
| 1013 | 860 | 870 | 966 | 1061 |
| 1060 | 877 | 923 | 993 | 1072 |
| 1067 | 923 | 935 | 1014 | 1103 |
| 1109 | 960 | 951 | 1059 | 1160 |
| 1151 | 994 | 958 | 1066 | 1187 |
| 1178 | 1059 | 993 | 1108 | 1194 |
| 1188 | 1102 | 1053 | 1151 | 1210 |
| 1211 | 1163 | 1062 | 1162 | 1267 |
| 1244 | 1194 | 1101 | 1177 | 1279 |
| 1257 | 1208 | 1141 | 1188 | 1296 |
| 1280 | 1230 | 1159 | 1194 | 1310 |
| 1298 | 1279 | 1187 | 1210 | 1341 |
| 1320 | 1298 | 1206 | 1231 | 1444 |
| 1358 | 1312 | 1216 | 1243 | 1515 |
| 1423 | 1341 | 1237 | 1279 | 1598 |
| 1449 | 1365 | 1276 | 1298 | 1632 |
| 1461 | 1442 | 1294 | 1320 | 2837 |
| 1477 | 1473 | 1309 | 1357 | 2945 |
| 1593 | 1513 | 1339 | 1422 | 2997 |
| 1601 | 1587 | 1439 | 1447 | 3063 |
| 1635 | 1601 | 1454 | 1517 | 3079 |
| 2833 | 1630 | 1514 | 1590 | 3101 |
| 2934 | 2841 | 1596 | 1600 | 3409 |
| 2953 | 2952 | 1633 | 1633 | |
| 2991 | 2986 | 2833 | 2833 | |
| 3012 | 3001 | 2946 | 2937 | |
| 3052 | 3057 | 2989 | 2952 | |
| 3069 | 3085 | 2997 | 2987 | |
| | 3413 | 3003 | 3001 | |
| | | 3053 | 3012 | |
| | | 3079 | 3058 | |
| | | 3095 | 3068 | |
| | | 3405 | 3085 | |
| | | | 3415 | |

FIG. 19

Dissolution Profiles of Pterostilbene Form I (Circles) and Form II (Squares) in Water at 25 °C (Open Symbols) and 37 °C (Filled Symbols), n = 3

KEY INTERMEDIATE FOR THE PREPARATION OF STILBENES, SOLID FORMS OF PTEROSTILBENE, AND METHODS FOR MAKING THE SAME

CROSS REFERENCE TO RELATED APPLICATIONS

The present application (1) is a continuation-in-part of International Patent Application No. PCT/IN09/000,313, filed Jun. 1, 2009, which claims the benefit of Indian Patent Application No. 1766/CHE/2008, filed Jul. 23, 2008, (2) is a continuation-in-part of International Patent Application No. PCT/US10/22285, filed Jan. 27, 2010, which also claims the benefit of Indian Patent Application No. 1766/CHE/2008 and PCT/IN/09/000313, and (3) claims the benefit of Indian Patent Application No. 741/CHE/2010, filed Mar. 22, 2010, all of which are hereby incorporated by reference.

BACKGROUND OF THE INVENTION

1. Field of Invention

The present invention relates to the preparation of 3,5-Dimethoxy-4'-O-tetrahydropyranylstilbene, which is a key intermediate for the synthesis of Stilbenes such as Pterostilbene and Resveratrol. The present invention also relates to new crystalline compounds of Pterostilbene, more particularly, the invention relates to Pterostilbene polymorphs, therapeutic uses of those Pterostilbene polymorphs, and pharmaceutical/nutraceuticals compositions containing them.

2. Description of the Related Art

Pterostilbene (trans-3,5-dimethoxy-4'-hydroxystilbene) is a naturally occurring stilbenoid compound that is a structural analog of Resveratrol. The chemical structures of Pterostilbene and Resveratrol are:

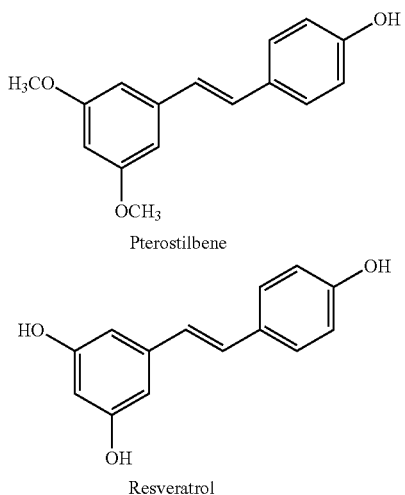

Methods for preparing stilbenes such as Pterostilbene and Resveratrol are known in the art. JMC, 2002, 45 (12), 2534-2542 discloses a process for preparing Pterostilbene by: condensing 3,5-Dimethoxybenzyltriphenylphosphonium bromide with 4-(tert-butyldimethylsilyloxy)benzaldehyde in tetrahydrofuran yields 4'-(tert-butyldimethyl silyloxy)-3,5-dimethoxystilbene; and treating 4'-(tert-Butyldimethylsilyloxy)-3,5-dimethoxystilbene with tetrabutyl ammonium fluoride affords Pterostilbene.

CN 1948274 discloses a process for preparing Pterostilbene by: condensing 4-benzyloxybenzaldehyde with 3,5-dimethoxybenzyl phosphonate in presence of sodium hydride yields 3,5-dimethoxy-4'-benzyloxystilbene; and debenzylating 3,5-dimethoxy-4'-benzyloxystilbene with aluminum chloride and N,N-dimethylaniline in dichloromethane yields Pterostilbene.

CN 1955153 discloses a process for preparing Pterostilbene by: condensing 3,5-Dimethoxybenzyl phosphonic acid diethyl esters with hydroxy benzaldehyde methoxymethyl ethers affords the substituted 3,5-Dimethoxy-4'-methoxymethyloxystyrylbenzene; and treating 3,5-Dimethoxy-4'-methoxymethyloxystyrylbenzene dissolved in methanol with Pyridinium p-toluene sulfonate (PPTS) yields Pterostilbene.

Indian Journal of Chemistry, Section B: 2002, 41B (11), 2395-2398 discloses a process for preparing Resveratrol by: treating Tri-O-methyl (—OMe) or tri-O-benzyl (—OCH$_2$Ph) Resveratrol with BBr$_3$ in CH$_2$Cl$_2$ yields Resveratrol.

U.S. Pat. No. 7,253,324 discloses a process for preparing Resveratrol by: treating Tri-O-methyl(—OMe) or tri-O-benzyl (—OCH$_2$Ph) Resveratrol with AlCl$_3$/N,N-dimethylaniline yields Resveratrol.

The limitations of the above methods are scalability and difficulty in selective deprotection to prepare Pterostilbene and use of expensive reagents for protection and/or low yields obtained in the process. So there is a need of the industry to have a process that is scalable and without using expensive reagents.

According to the present invention there is provided a convenient process for the preparation of stilbene with desired purity and yield by using a novel intermediate 3,5-Dialkyl-4'-O-tetrahydropyranylstilbene.

Both Resveratrol and Pterostilbene have been reported to exhibit a range of biological activities including anti-cancer, antioxidant, anti-inflammatory and other potential health benefits. Pterostilbene is found in nature in a variety of grapes and berries as well as plants commonly used in traditional folk medicine. Significant interest in Pterostilbene has been generated in recent years due to its perceived health benefits, leading to increased consumption of foods that contain the compound such as grapes and berries.

While limited solid-state characterization has been reported for Resveratrol, solid-state properties of Pterostilbene have not been thoroughly studied to date. The compound has been noted to have poor solubility in water, making it difficult to incorporate in food extracts or supplements ("nutraceuticals") (Lopez-Nicolas, J. M.; Rodriguez-Bonilla, P.; Mendez-Cazorla, L.; Garcia-Carmona, F., *Physicochemical Study of the Complexation of Pterostilbene by Natural and Modified Cyclodextrins*, Journal of Agricultural and Food Chemistry 2009, 57, (12), 5294-5300.). In addition, Pterostilbene exhibits poor bioavailability and is easily oxidized by various enzymes (Pezet, R., *Purification and characterization of a 32-kDa laccase-like stilbene oxidase produced by Botrytis cinerea*, FEMS Microbiol. Lett. 1998, 167, 203-208, and Breuil, A. C.; Jeandet, P.; Adrian, M.; Chopin, F.; Pirio, N.; Meunier, P.; Bessis, R., *Characterization of a pteristilbene dehydrodimer produced by laccase of Botrytis cinerea*, Phytopathology 1999, 89, (298-302).). The melting point has been reported as 82° C. (Mallavadhani, U. V.; Sahu, G., *Pterostilbene: A Highly Reliable Quality-Control Marker for the Ayurvedic Antidiabetic Plant 'Bijasar'*, Chromatographia 2003, 58, 307-312.) Efforts to improve the solubility of Pterostilbene have focused on formulation approaches such as by using cyclodextrins (Lopez-Nicolas 2009).

It is well established that solid-state properties of compounds can significantly affect their ability to become viable commercially such as by way of becoming an active pharmaceutical or nutraceutical ingredient in a formulated product. Properties, such as solubility, chemical stability, and physical stability, are known to vary, often significantly, between different solid forms of a compound.

SUMMARY AND OBJECTS OF THE INVENTION

The principal objects of the present invention include providing a process for the preparation of Stilbenes, specifically Pterostilbene, and forming various solid forms of Pterostilbene, including amorphous and polymorphic forms, and dosage forms, and to use the same for treatment of disease or for nutritional supplementation purposes.

It is another object of the present invention to provide a process for the preparation of stilbenes by deprotection 3,5-Dialkyl-4'-O-tetrahydropyranyl stilbene of formula 1, Formula 1

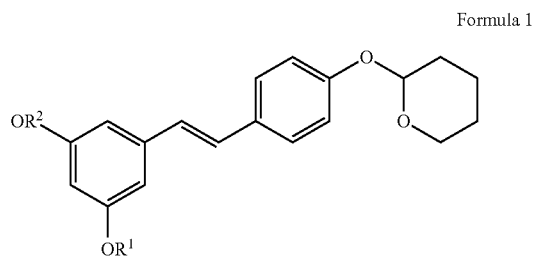

Where $R^1$ and $R^2$ each independently represent hydrogen, lower alkyl or aralkyl.

Another object of the present invention is to provide a process for the preparation of 3,5-Dialkyl-4'-O-tetrahydropyranyl stilbene.

The term "solid form" is often used to refer to a class or type of solid-state material. For example, the term "polymorph" when used to describe solid-state compounds refers to two or more compounds having the same chemical formula but differing in solid-state structure. When polymorphs are elements, they are termed allotropes. Carbon possesses the well known allotropes of graphite, diamond, and buckminsterfullerene. Polymorphs of molecular compounds, such as active pharmaceutical or nutraceutical ingredients, are often prepared and studied in order to identify compounds meeting scientific or commercial needs including, but not limited to improved solubility, dissolution rate, hygroscopicity, and stability.

Other solid forms include solvates and hydrates. A solvate is a compound wherein a solvent molecule is present in the crystal structure together with another compound. When the solvent is water, the solvent is termed a hydrate. Solvates and hydrates may be stoichiometric or non-stoichiometric. A unique XRPD pattern was observed from a number of crystallization experiments involving dioxane, suggesting a potential dioxane solvate. The materials produced in those experiments appeared to be a mixture, including one of the pterostilbene forms.

Thus, another object of the present invention is to provide five crystalline polymorphs of Pterostilbene, disclosed herein and characterized by various analytical techniques. In addition, x-ray amorphous Pterostilbene and a t-butanol solvate of Pterostilbene are disclosed. The polymorphs, amorphous form, and t-butanol solvate are all solid forms of Pterostilbene.

As used herein, the word "characterize" means to identify a collection of data which may be used to identify a solid form. The process by which solid forms are characterized involves analyzing data collected on the forms so as to allow one of ordinary skill in the art to distinguish one solid form from other solid forms containing the same active pharmaceutical or nutraceutical ingredient. Chemical identity of solid forms can often be determined with solution-state techniques such as 13C NMR or 1H NMR. While it may help identify the active agent, such as an active pharmaceutical or nutraceutical ingredients, and a solvent molecule for a solvate, such solution-state techniques do not provide information about the solid state. There are, however, solid-state analytical techniques that can be used to provide information about solid-state structure and differentiate among solid forms such as polymorphs including single crystal x-ray diffraction, powder x-ray diffraction, solid-state 13C NMR, Raman spectroscopy, and thermal techniques such as Differential Scanning calorimetry (DSC), melting point, and hot stage microscopy.

To characterize a polymorph of a compound, one may, for example, collect x-ray powder diffraction data on solid forms of the compound and compare the x-ray powder diffraction peaks of the forms. When only two polymorphic forms—I and II—are compared and one finds a peak in a Form I pattern at an angle where no peaks appear in the Form II pattern, then that peak, for that chemical compound, distinguishes Form I from Form II and further acts to characterize Form I. When more forms are present, then the same analysis is also done for the other forms. Thus, to characterize Form I against the other forms, one would look for peaks in Form I at angles not present in the x-ray powder diffraction patterns of the other forms. One may utilize more than one peak to characterize a form as it is possible that a peak in Form I is not present in Form II, but is present in Form III. The collection of peaks which distinguish Form I from the other known forms is a collection of peaks which may be used to characterize Form I. If, for example, two peaks characterize a form then those two peaks can be used to identify the presence of that form. Those of ordinary skill in the art will recognize that there are often multiple ways, including multiple ways using the same analytical technique, to characterize polymorphic forms. For example, one may find that three x-ray powder diffraction peaks characterize a form. Additional peaks could also be used, but are not necessary, to characterize the form up to and including an entire diffraction pattern. Although all the peaks within an entire diffractogram may be used to characterize such a form, one may instead, and typically does as disclosed herein, use a subset of that data to characterize the form.

An x-ray powder diffraction plot is an x-y graph with °2θ (diffraction angle) on the x-axis and intensity on the y-axis. The peaks within this plot may be used to characterize a crystalline solid form. The data is often represented by the position of the peaks on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the art to characterize solid forms such as polymorphs.

As with any data measurement, there is variability in x-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline solid form. Likewise, different software packages process x-ray data differently and this also leads to variability. These and other sources of variability are known to those of ordinary skill in the pharmaceutical arts.

Due to such sources of variability, it is common to recite x-ray diffraction peaks using the word "about" prior to the peak value in °2θ which presents the data to within 0.1 or 0.2°2θ of the stated peak value depending on the circumstances. The x-ray powder diffraction data corresponding to the solid forms of Pterostilbene of the disclosure were collected on instruments which were routinely calibrated and operated by skilled scientists. Accordingly, the variability associated with these data would be expected to be closer to ±0.1 °2θ than ±0.2°2θ and indeed likely less than 0.1. All x-ray powder diffraction peaks cited herein have are reported with a variability on the order of ±0.1°2θ and are intended to be reported with such a variability whenever disclosed herein. For peak selection purposes, characteristic peaks for Pterostilbene were selected from peaks which were separated by up to (but not including) 0.2°2θ from peaks in other polymorphic forms of Pterostilbene. Therefore, when a peak is reported at an angle in a diffraction pattern of a first form but not present in a diffraction pattern(s) of a second or more forms, then no peak is identified less than 0.2°2θ away from that angle in the diffraction patterns of those second or more forms.

In the instant disclosure, the Applicants identified five polymorphs of Pterostilbene. X-ray powder diffraction patterns were collected for each of the polymorphs. The peaks for each of the powder patterns were identified and compared with peaks for the patterns representing the other forms to look for peaks present for each form but not present in the others to within, experimental variation. Thus, x-ray powder diffraction data to characterize the different polymorphs were identified. A preference was given for peaks with lower °2θ on the x-axis of each diffraction pattern due to the greater separation between peaks generally in that region of the diffractograms.

Single-crystal x-ray diffraction provides three-dimensional structural information about the positions of atoms and bonds in a crystal. It is not always possible or feasible, however, to obtain such a structure from a crystal, due to, for example, insufficient crystal size or difficulty in preparing crystals of sufficient quality for single-crystal x-ray diffraction.

Raman spectroscopy is another technique that may be used to characterize solid forms together with or separately from x-ray powder diffraction. Raman spectroscopy is a scattering technique wherein a light source, often a laser, is used to interact with a sample. Raman scattered light, which is light that interacts with the sample, is collected by a detector and the intensity of that light can be plotted versus the "wavenumber" of the light to obtain a spectrum. A wavenumber has the units of inverse centimeters (cm-1). Wavenumbers are plotted on the x-axis of a Raman spectrum with intensity on the y-axis. As with x-ray powder diffraction plots, Raman peaks are recorded by reference to their x-axis (wavenumber) position rather than their intensity. Variation in the position of Raman peaks also exists and may be due to sample conditions as well as data collection and processing. The typical variability in Raman spectra reported herein is on the order plus or minus 2.0 cm-1. Thus, the use of the word "about" when referencing Raman peaks is meant to include this variability and all Raman peaks disclosed herein are intended to be reported with such variability.

Using the same general procedure for variability as with x-ray powder diffraction, the Raman peaks used to characterize the polymorphs of Pterostilbene are selected so that they distinguish the forms from one another. Peaks present in one form but not present in another are peaks that may be used to distinguish with respect to that form. For peak selection purposes, peak separation between peaks among forms was chosen to be 4 cm-1, which is the resolution of the Raman instrument used. Therefore, for purposes of the disclosure, when a peak is reported as present in a first form but not in second or more forms, it is intended to mean that there is no peak identified less than 4 cm-1 away from that peak in those second or more forms.

Thermal methods are another typical technique to characterize solid forms. Different polymorphs of the same compound often melt at different temperatures. Thus, the melting point of a polymorph, as measured by methods such as capillary melting point, DSC, and hot stage microscopy, alone or in combination with techniques such as x-ray powder diffraction, Raman spectroscopy, or both, may be used to characterize polymorphs or other solid forms.

As with any analytical technique, melting points determinations are also subject to variability. Common sources of variability, in addition to instrumental variability, are due to colligative properties such as the presence of other solid forms or other impurities within a sample whose melting point is being measured.

BRIEF DESCRIPTION OF THE DRAWINGS

FIG. 19 is a Raman peak list for Forms I-V of Pterostilbene; and

DETAILED DESCRIPTION OF THE INVENTION

Figure 1:
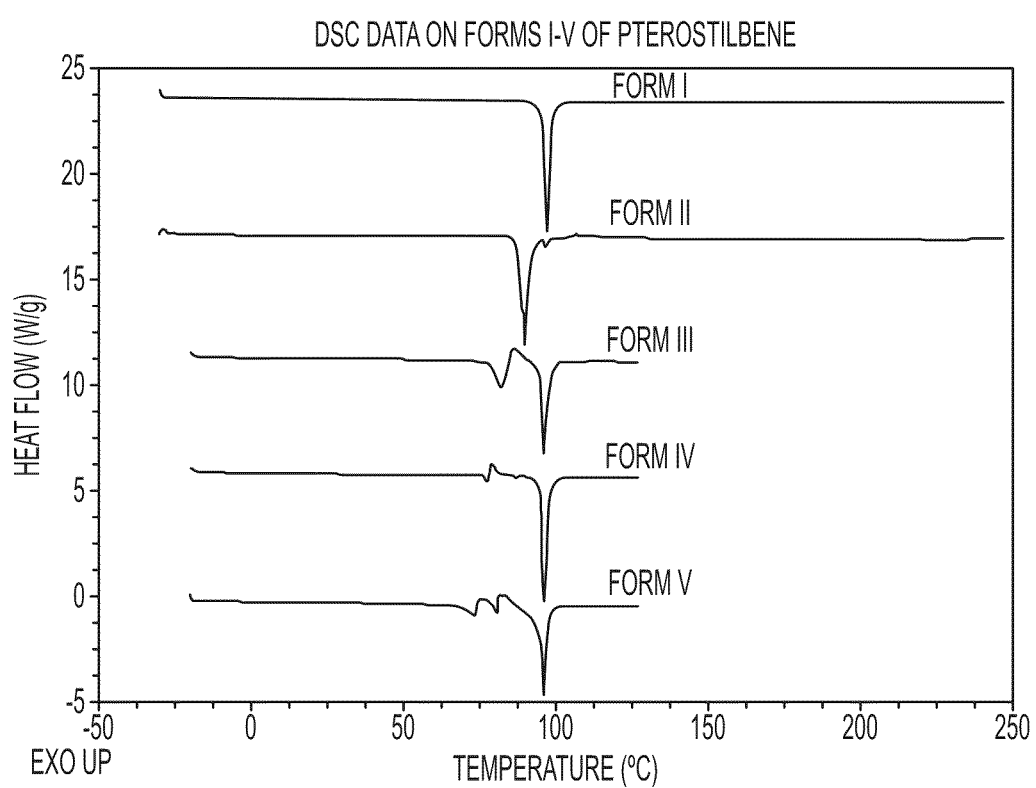
FIG. 1 is a DSC stack plot for Forms I-V of Pterostilbene.

Several preferred embodiments of the present invention are described for illustrative purposes, it being understood that the invention may be embodied in other forms not specifically shown in the drawings. The figures will be described with respect to the structure and functions that achieve one or more of the objects of the invention and/or receive the benefits derived from the advantages of the invention as understood by persons skilled in the art or explicitly set forth herein.

In accordance with the present invention, preparation of Stilbenes comprising the steps of: condensing 3,5-dialkyl-benzyl phosphonates with 4'-O-tetrahydropyranyl benzaldehyde to get 3,5-Dialkyl-4'-O-tetrahydropyranylstilbene; and deprotecting the obtained 3,5-Dialkyl-4'-O-tetrahydropyranylstilbene yields stilbene. The reaction steps are illustrated in scheme-1 below.

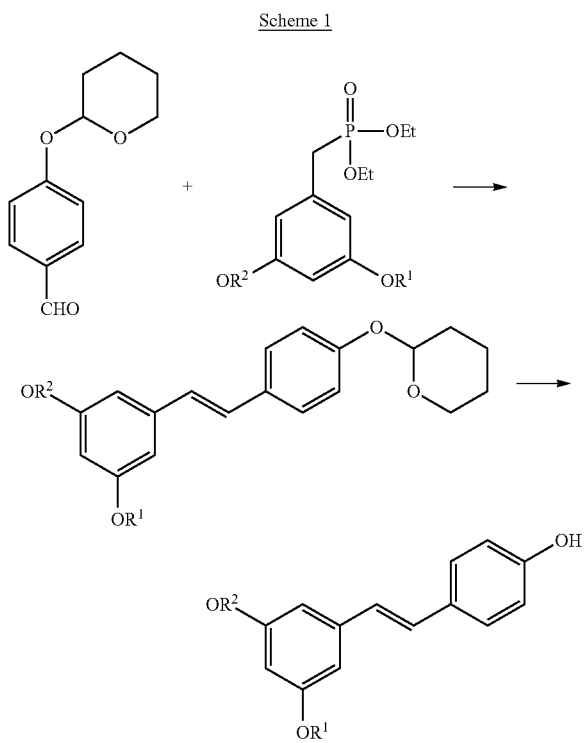

Scheme 1

Wherein $R^1$ and $R^2$ independently represent hydrogen, lower alkyl or aralkyl.

In the process as described above, the preferable Stilbenes are Pterostilbene and Resveratrol.

Condensation of 3,5-dialkylbenzyl phosphonates with 4'-O-tetrahydropyranyl benzaldehyde is carried out in presence of a base, preferably sodium hydride at a temperature ranging from room temperature to reflux temperature of the solvent used.

Deprotection of the above obtained compound, i.e., 3,5-Dialkyl-4'-O-tetrahydropyranylstilbene is carried out in presence of a suitable deprotecting agent selecting from PPTS, aluminum chloride, N,N-dimethylaniline and mixtures thereof.

In a specific embodiment of the present invention 3,5-Dialkyl-4'-O-tetrahydropyranylstilbene is found to be novel and it can be a key intermediate for the preparation of Stilbenes, preferably Pterostilbene and Resveratrol.

In another embodiment of the present invention 3,5-Dialkyl-4'-O-tetrahydropyranylstilbene is prepared by condensing 3,5-dialkylbenzyl phosphonates with 4'-O-tetrahydropyranyl benzaldehyde to get 3,5-alkyl-4'-O-tetrahydropyranylstilbene. In this process, the condensation may be carried in presence of a base, wherein the preferred base is sodium hydride, and the reaction is carried out in a solvent, preferably tetrahydrofuran.

In another embodiment of the present invention, Pterostilbene can be prepared by deprotecting the 3,5-Dimethoxy-4'-O-tetrahydropyranylstilbene using pyridinium p-toluene sulfonate (PPTS) in an alcoholic solvent, preferably methanol. The reaction may be carried out at from room temperature to the reflux temperature of the solvent used.

In another embodiment of the present invention, Resveratrol can be prepared by deprotecting the 3,5-Dimethoxy-4'-O-tetrahydropyranylstilbene using Aluminum chloride and N,N-Dimethylaniline in an organic solvent, preferably toluene. The reaction may be carried out at from room temperature to the reflux temperature of the solvent used.

TABLE 1

Interconversion Experiments

| Forms | Observations | XRPD Result |
|---|---|---|
| I/II | Needles/Blades | Form I |
| I/V | Needles/Blades | Form I |
| II/III/IV/V | — | Form II |
| I/II/IV | Needles/Blades | Form I + II |
| I/D | Needles/Blades | Form I |
| I/IV | Needles/Blades | Form I |
| II/III | — | Form II |
| II/V | Blades | Form II |
| II/IV | — | Form I |
| II/D w/I | — | Form I |
| II/IV | — | Form II |
| II/IV/D w/I | — | Form I |
| II/IV/V | — | Form II |
| II/IV/V | — | Form II |
| V/D w/I | — | Form I + II |
| IV/V | — | Form II + minor Form I |

Form D in Table 1 is a solid form of Pterostilbene which was not fully characterized.

Thermodynamic stability relationships of known forms of Pterostilbene were studied by calculating the enthalpy of fusion for each form (from DSC data, Table 4) and through slurry interconversion experiments in toluene in Table 1. Form I material exhibited the highest enthalpy of fusion and all interconversion experiments involving Form I material resulted in Form I, with the exception of one experiment that yielded a mixture of Forms I and II. The melting point of Form I was higher than that of Forms II-V, (Table 4). Therefore, Form I is believed to be the thermodynamically stable crystal form of Pterostilbene from absolute zero to its melting point and is monotropically related to the other known forms.

Based on additional slurry interconversion experiments including only Forms II-V, Form II appears to be thermodynamically favored compared to Forms III-V under ambient conditions.

TABLE 2

Indexing Solutions for Forms I, II, III, and V

| | Form | | | |
|---|---|---|---|---|
| | Form I | Form II | Form III | Form V |
| Family and Space Group | Monoclinic P2$_1$/c (#14) | Monoclinic P2$_1$/n (#14) | Monoclinic P2$_1$/c (#14) | Monoclinic P2$_1$ (#4) or P2$_1$/m (#11) |
| Z'/Z | 2/8 | 1/4 | 1/4 | 2/4 or 1/4 |
| a (Å) | 15.461 | 9.546 | 15.742 | 11.089 |
| b (Å) | 5.798 | 4.116 | 11.073 | 7.176 |
| c (Å) | 30.819 | 33.668 | 7.622 | 17.202 |
| α (deg) | 90 | 90 | 90 | 90 |
| β (deg) | 93.29 | 93.16 | 94.10 | 99.52 |
| γ (deg) | 90 | 90 | 90 | 90 |
| Volume (Å$^3$/cell) | 2758.2 | 1320.8 | 1325.2 | 1350.0 |
| V/Z (Å$^3$/asym. unit) | 344.8 | 330.2 | 331.3 | 337.5 |
| Assumed composition | C$_{16}$H$_{16}$O$_3$ | C$_{16}$H$_{16}$O$_3$ | C$_{16}$H$_{16}$O$_3$ | C$_{16}$H$_{16}$O$_3$ |
| Density (g/cm$^3$)$^a$ | 1.23 | 1.29 | 1.29 | 1.26 |

The laboratory XRPD patterns of Pterostilbene Forms I, II, III, and V were indexed using a combination of commercially available and proprietary software. The indexed solutions were verified and illustrated using publicly available Check-Cell software. Successful indexing of these patterns indicated that the samples were composed primarily of a single crystalline phase. Space groups consistent with the assigned extinction symbols, unit cell parameters, and derived quantities are tabulated in Table 3. No attempts to confirm the indexing solutions with molecular packing were performed. The indexing solution for Form II is consistent with the experimental single crystal structure solution shown in Table 3.

TABLE 3

Single Crystal Data for Form II

| | |
|---|---|
| Empirical formula | C$_{16}$H$_{16}$O$_3$ |
| MW | 256.29 |
| Crystal system | Monoclinic |
| Space group, Z | P2(1)/n, 4 |
| a, Å | 9.5187 (13) |
| b, Å | 4.0022 (6) |
| c, Å | 33.417 (5) |
| α, ° | 90 |
| β, ° | 93.215 (5) |
| γ, ° | 90 |
| Volume, Å$^3$ | 1271.0 (3) |
| Density, g/cm$^3$ | 1.339 |
| Temperature, K | 120 (2) |
| X-ray wavelength | 0.71073 |
| μ, mm$^{-1}$ | 0.0.92 |
| F(000) | 544 |
| θ$_{min}$, ° | 2.44 |
| θ$_{max}$, ° | 32.56 |
| Reflections | |
| collected | 12175 |
| independent | 4331 |
| observed | 4978 |
| Threshold expression | >2σ(l) |
| R$_1$ (observed) | 0.0494 |
| wR$_2$ (all) | 0.1460 |

TABLE 4

Thermal Data for Polymorphs of Pterostilbene with Hot Stage Microscopy, DSC, TGA, and WVS

| Form | Melt onset (° C.) | Enthalpy of fusion (kJ/mol) | % weight loss (at 150° C.) | Sorption/Desorption (5-95-5% RH, in weight %) |
|---|---|---|---|---|
| I | 94-96 | 25.6/26.4 | 0.5 | 0.2/0.2 |
| II | 85-86 | 23.6/24.2 | 0.2 | 0.2/0.2 |
| III | 76-81 | 19.2 | 0.2 | 0.6/0.5 |
| IV | 76 | — | 0.2 | 0.5/0.5 |
| V | 71 | — | 0.4 | 0.8/0.5 |

In Table 4, for Form I, the 26.4 kJ/mol value for the enthalpy of fusion was calculated from a single 10° C./min pattern whereas the 25.6 kJ/mol value was calculated as an average from three 50° C./min patterns. DSC results for Form III indicated a melt onset at 76° C., while HSM results indicated it was 81° C. Material decomposition was observed upon heating above approximately 170° C. The minor weight loss observed up to 150° C. was attributed to loss of residual solvent. FIG. 1 is a DSC stack plot for Forms I-V of Pterostilbene.

In one aspect of the disclosure, the invention provides for seven solid forms of Pterostilbene: polymorphs of Pterostilbene (Forms I, II, III, IV, and V), a t-butanol solvate of Pterostilbene, and an x-ray amorphous form of Pterostilbene.

In another aspect of the disclosure, the invention provides for processes for making each of the solid forms of Pterostilbene which are disclosed herein.

In yet another aspect of the disclosure, substantially pure solid forms of Pterostilbene forms I, II, III, V and the x-ray amorphous form are herein provided.

In a further aspect of the disclosure, formulations of solid forms of Pterostilbene are provided.

In another aspect of the disclosure, methods of administering solid forms of Pterostilbene are herein provided.

Figure 2:
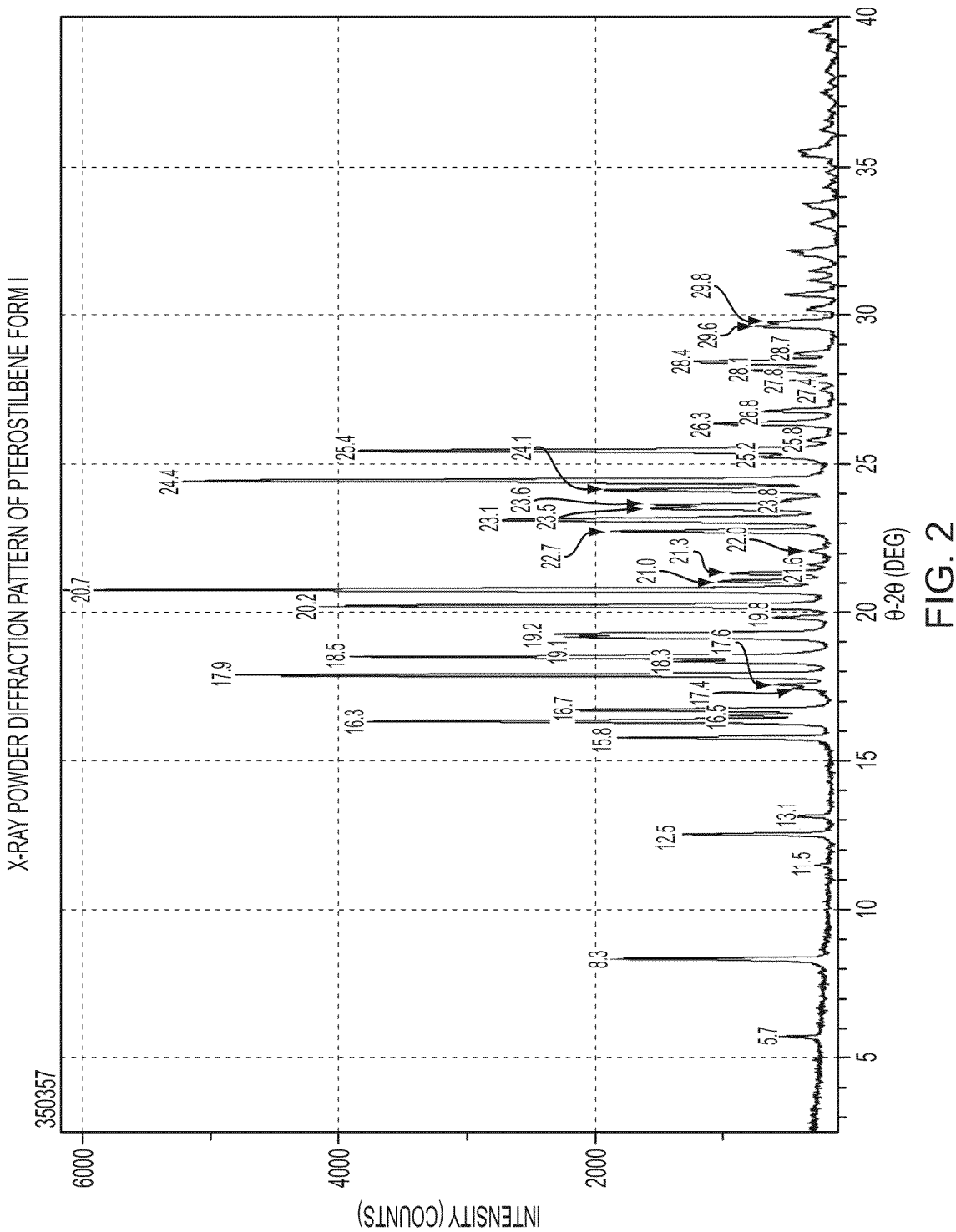
FIG. 2 is an x-ray powder diffraction pattern of Pterostilbene Form I.
Figure 5:
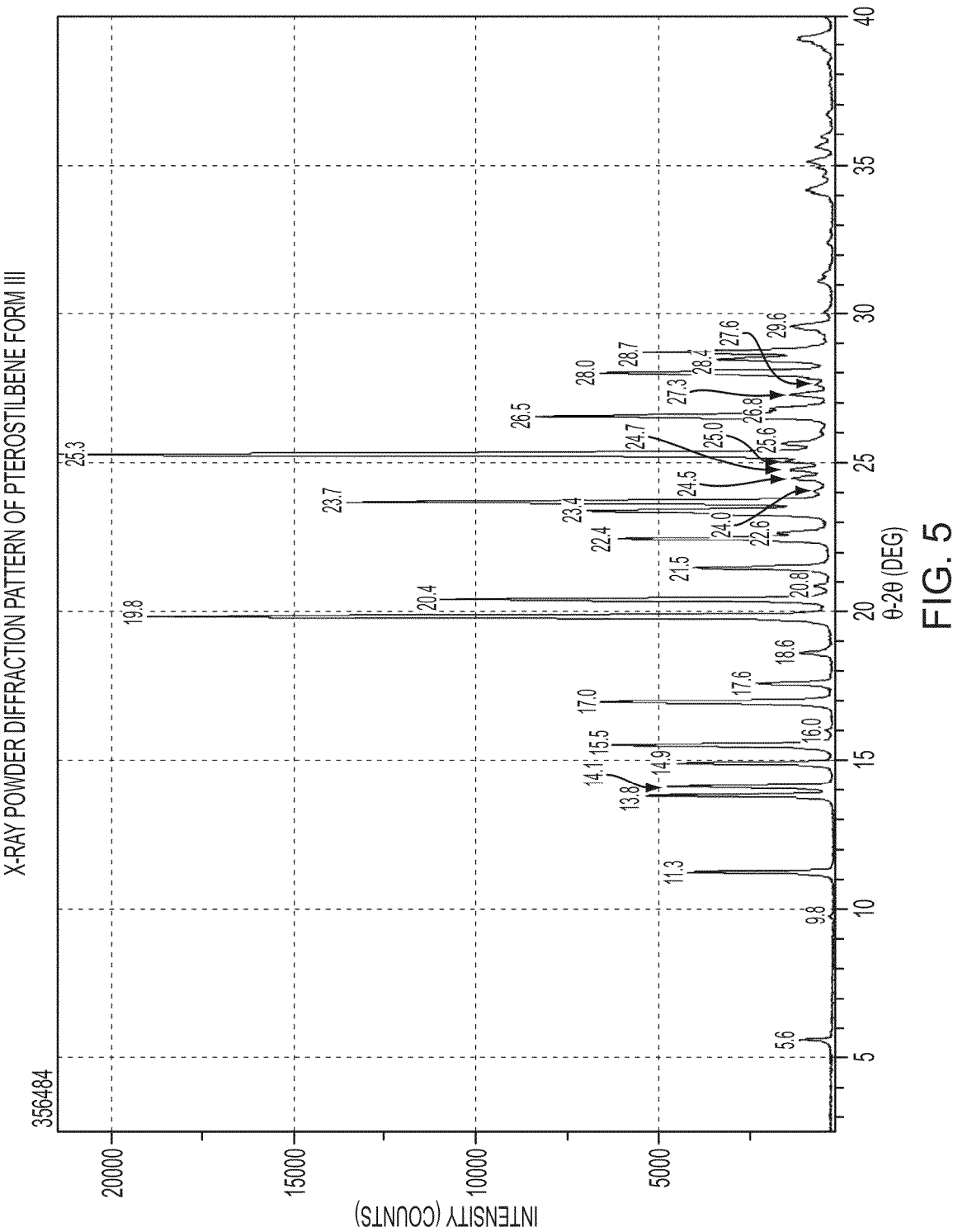
FIG. 5 is an x-ray powder diffraction pattern of Pterostilbene Form III.

FIG. 2 is a powder x-ray diffraction pattern of Form I of Pterostilbene and shows the peak locations of many of the peaks within the diffractogram. In order to differentiate Form I of Pterostilbene from the other polymorphs of Pterostilbene, the peaks were evaluated and compared to the peaks of the other forms described herein. As is apparent from FIG. 2, the density of peaks increases after about 15-17°2θ. Thus, emphasis was placed on peaks less than or equal to about 15-17°2θ. The peak at about 8.3°2θ is present in Form I but not in Form III or Form II. The peak at about 16.7°2θ is present in Form I but is not present in Form V or Forms II or III. It is further believed that the Form IV prepared in the disclosure is contaminated with some amount of Form I. Thus, Form I and Form IV as prepared (a potential mixture of Form IV and Form I) can be distinguished based on melting point. A phase pure or substantially phase pure Form IV would likely be distinguishable from a phase pure or substantially phase pure Form I. Indeed, the peak found at about 5.7°2θ in FIG. 5 is likely due to the presence of Form I as evidenced by data from indexing the various forms. Form IV as prepared was measured to have a melting point of about 76° C. whereas Form I was measured to have a melting point of about 94-96° C. Thus, Form I can be characterized by peaks at about 8.3 and 16.7°2θ as well as a melting point of about 94-96° C. Although not necessary, additional peaks present in the diffractogram may also be used to characterize Form I. For example one or more of the peaks at about 12.5 and 15.8°2θ could additionally be used to characterize the form. It is possible, though not necessary, to also use higher angle peaks to further characterize the form.

Figure 3:
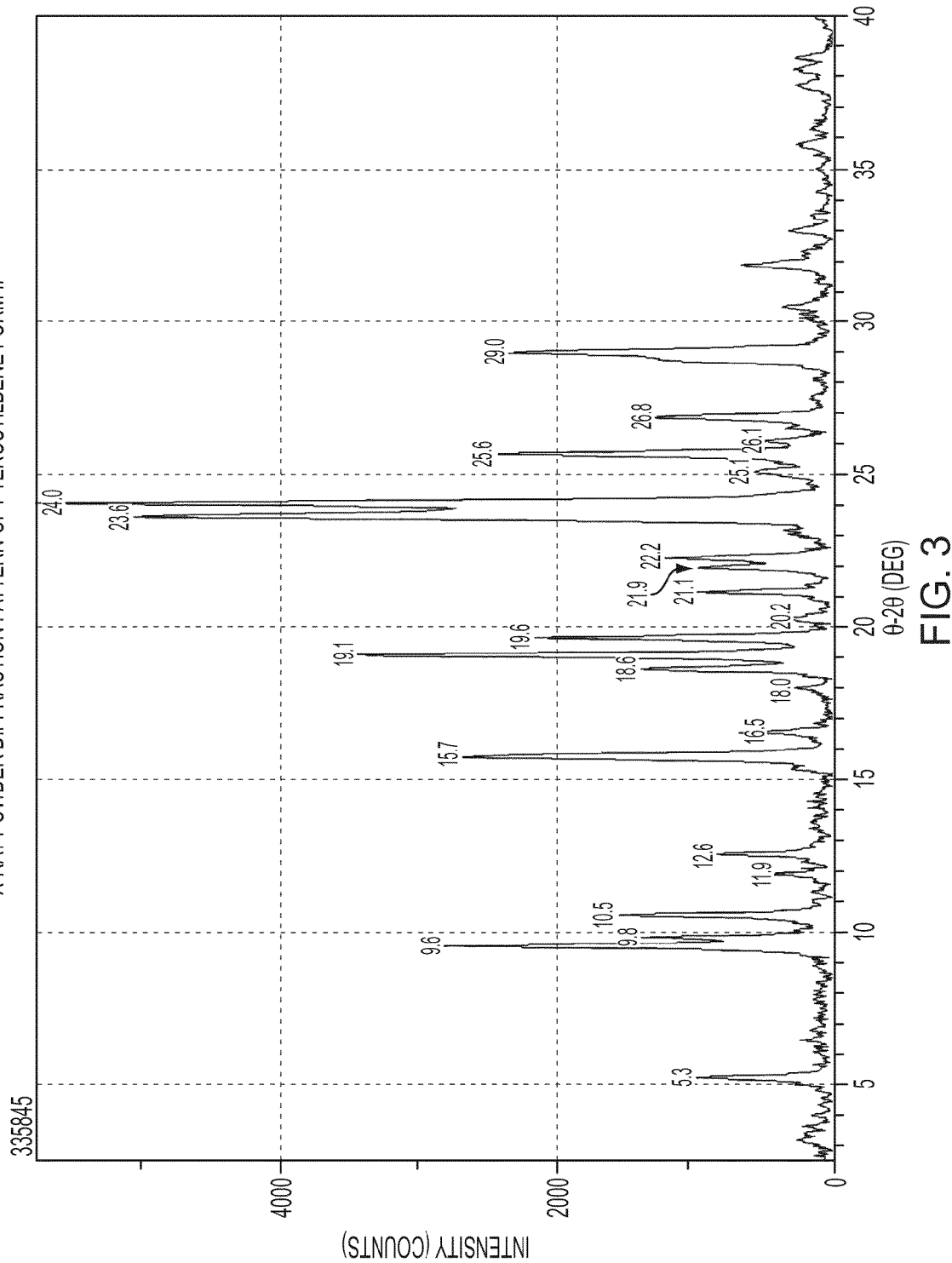
FIG. 3 is an x-ray powder diffraction pattern of Pterostilbene Form II.

FIG. 3 is the x-ray powder diffraction pattern of Pterostilbene Form II and shows the peak locations of many of the peaks within the diffractogram. In order to differentiate Form II of Pterostilbene from the other polymorphs of Pterostilbene, the peaks were evaluated and compared to the peaks of the other forms described herein. As is apparent from FIG. 3, the density of peaks increases after about 15-17°2θ. Thus, emphasis was placed on peaks less than about 15-17°2θ. The peak at about 5.3°2θ is not present in Forms I and Form IV. Form II possesses a peak at about 10.5°2θ which is not present in Form III, Form I, or Form IV. The peak at about 9.6°2θ in Form II is not present in Form V or Forms I or IV. Thus, the peaks at about 5.3, 9.6, and 10.5°2θ characterize Form II. Although not necessary, additional peaks present in the diffractogram may also be used to characterize Form II. For example one or more of the peaks at about 12.6 and 15.7°2θ could additionally be used to characterize the form. It is possible, though not necessary, to also use higher angle peaks to further characterize the form.

Figure 4:
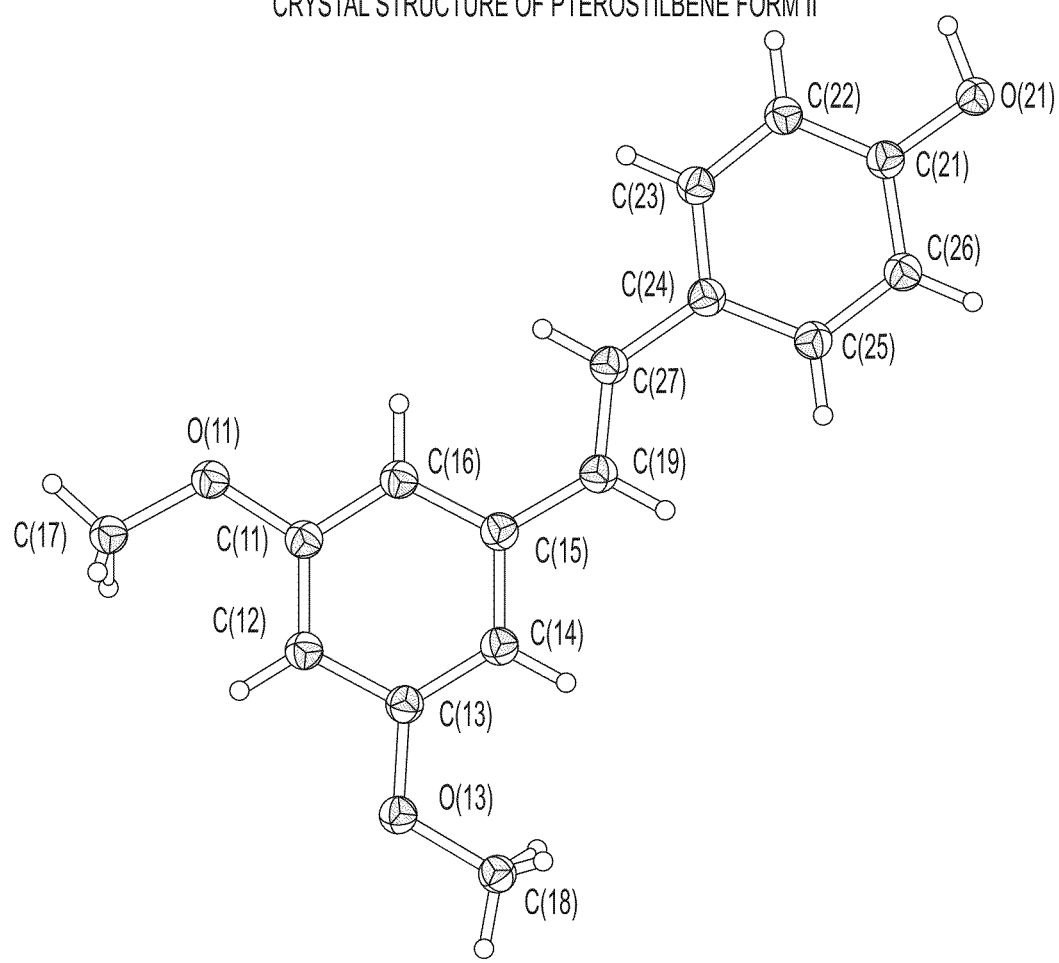
FIG. 4 is the crystal structure of Form II of Pterostilbene.

FIG. 4 illustrates x-ray crystal structure diagrams for Form II of Pterostilbene. The asymmetric unit of Pterostilbene Form II, contains one molecule of Pterostilbene in space group P2(1)/n. The molecules pack in single-stranded columns through O—H . . . O hydrogen bonds from the hydroxyl group to the oxygen of the methoxy group with an O21 . . . O11 distance of 2.8044(12) Å. The individual strands possess a left-handed helical pattern. Additional stabilizing π-π interactions exist between slipped-stacked Pterostilbene molecules with ring centroid:centroid distances of 4.0 Å. A summary of the crystallographic data collected on the single crystal data appear in Table 3.

Conformation that the x-ray structure was that of Form II Pterostilbene was achieved by simulating an XRPD pattern of the single crystal structure and comparing it to the experimental XRPD pattern of Form II which showed consistent agreement between the patterns confirming the identity of the crystal structure as that of Form II.

FIG. 5 is the x-ray powder diffraction pattern of Pterostilbene Form III. In order to differentiate Form III of Pterostilbene from the other polymorphs of Pterostilbene, the peaks were evaluated and compared to the peaks of the other forms described herein. As is apparent from FIG. 5, the density of peaks increases after about 20-22°2θ. Thus, emphasis was placed on peaks less than about 20-22°2θ. The peak at about 13.8°2θ distinguishes Form III from Form I as well as Forms II, IV, and V of Pterostilbene because that peak is not present in those forms. Thus, the peak at 13.8°2θ characterizes that form. Although not necessary, additional peaks present in the diffractogram may also be used to characterize Form III. For example one or more of the peaks at about 11.3, 14.1, 14.9, and 15.5°2θ could additionally be used to characterize the form. It is possible, though not necessary, to also use higher angle peaks to further characterize the form.

Figure 6:
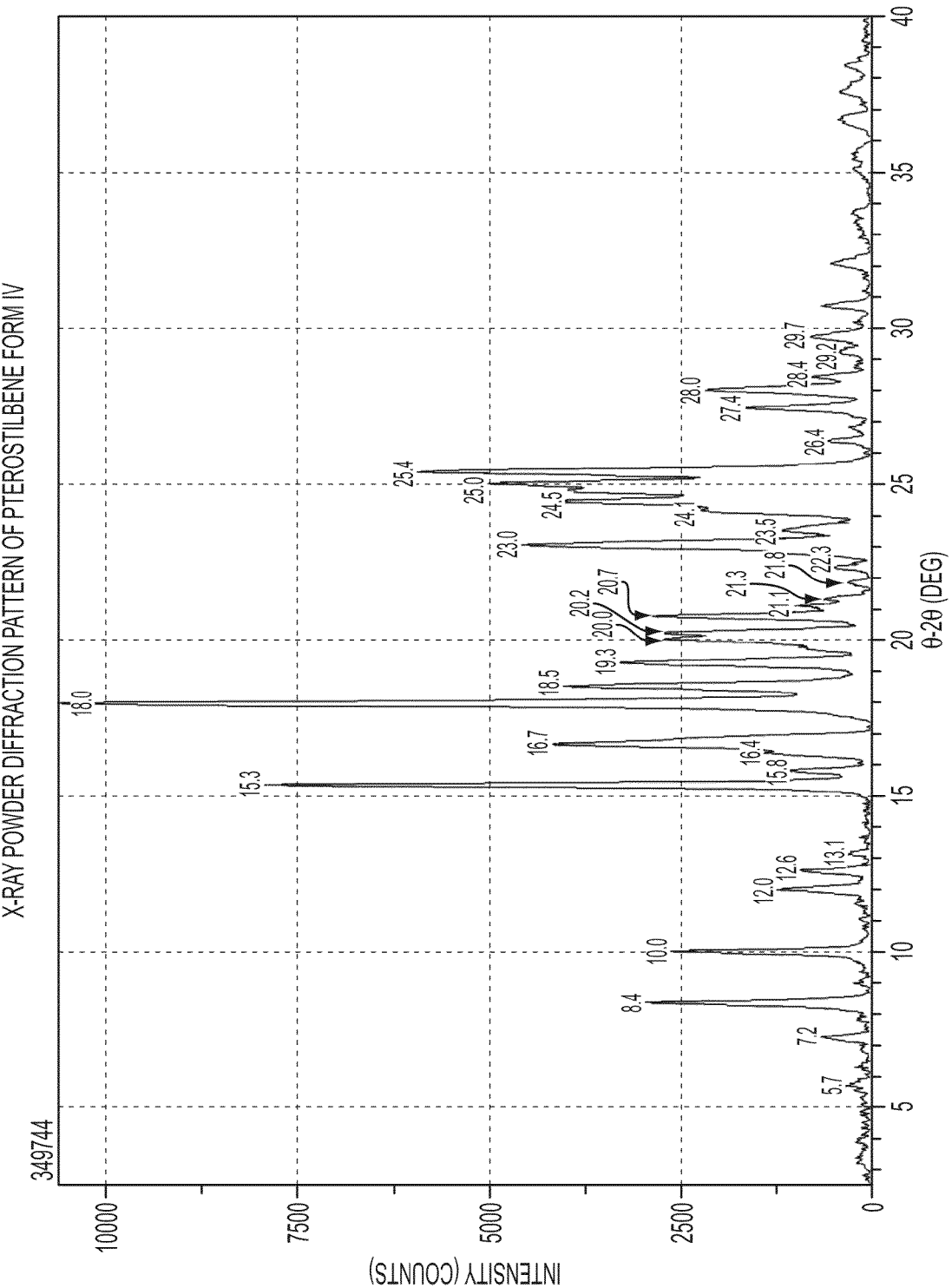
FIG. 6 is an x-ray powder diffraction pattern of Pterostilbene Form IV.

FIG. 6 is the x-ray powder diffraction pattern of Pterostilbene Form IV. In order to differentiate Form IV of Pterostilbene from the other polymorphs of Pterostilbene, the peaks were evaluated and compared to the peaks of the other forms described herein. As is apparent from FIG. 6, the density of peaks increases after about 15-17°2θ. Thus, emphasis was placed on peaks less than about 15-17°2θ. The peak at about 10.0°2θ distinguishes Form IV from Form I and from Form V. The peak at about 8.4°2θ distinguishes Form IV from Forms II, III, and V of Pterostilbene. Thus, the peaks at about 8.4 and 10.0°2θ characterize Form IV Pterostilbene. Although not necessary, additional peaks present in the diffractogram may also be used to characterize Form IV. For example one or more of the peaks at about 12.0 and 15.3°2θ could additionally be used to characterize the form. It is possible, though not necessary, to also use higher angle peaks to further characterize the form.

Figure 7:
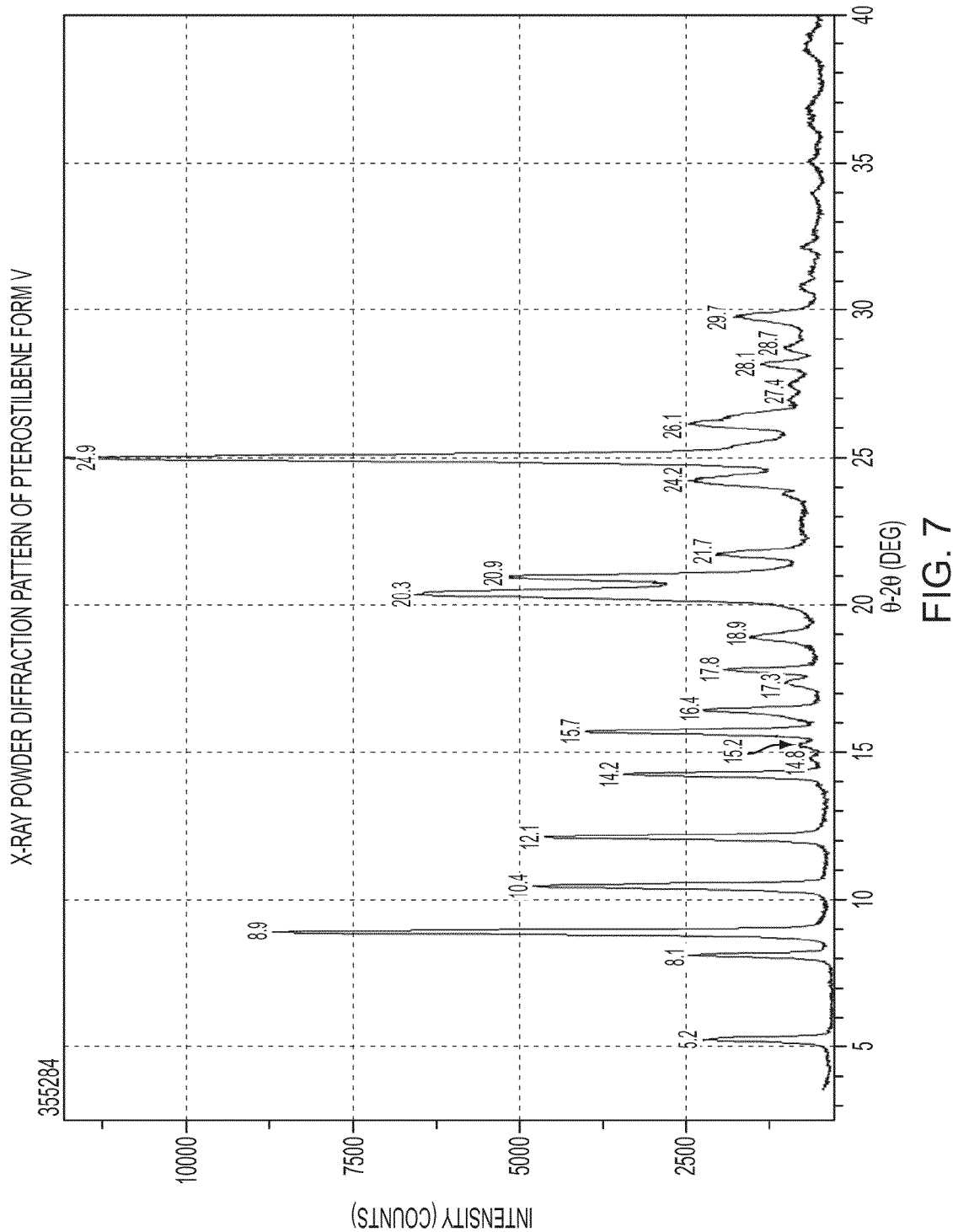
FIG. 7 is an x-ray powder diffraction pattern of Pterostilbene Form V.

FIG. 7 is the x-ray powder diffraction pattern of Pterostilbene Form V. In order to differentiate Form V of Pterostilbene from the other polymorphs of Pterostilbene, the peaks were evaluated and compared to the peaks of the other forms described herein. The peak at about 8.1°2θ distinguishes Form V from the other polymorphic forms of Pterostilbene. Thus, the peak at about 8.1°2θ characterize Form V. Although not necessary, additional peaks present in the diffractogram may also be used to characterize Form V. For example, one or more of the peaks at about 5.2, 8.9, 10.4, 12.1 and 14.2°2θ could additionally be used to characterize the form. It is possible, though not necessary, to also use higher angle peaks to further characterize the form.

Figure 8:
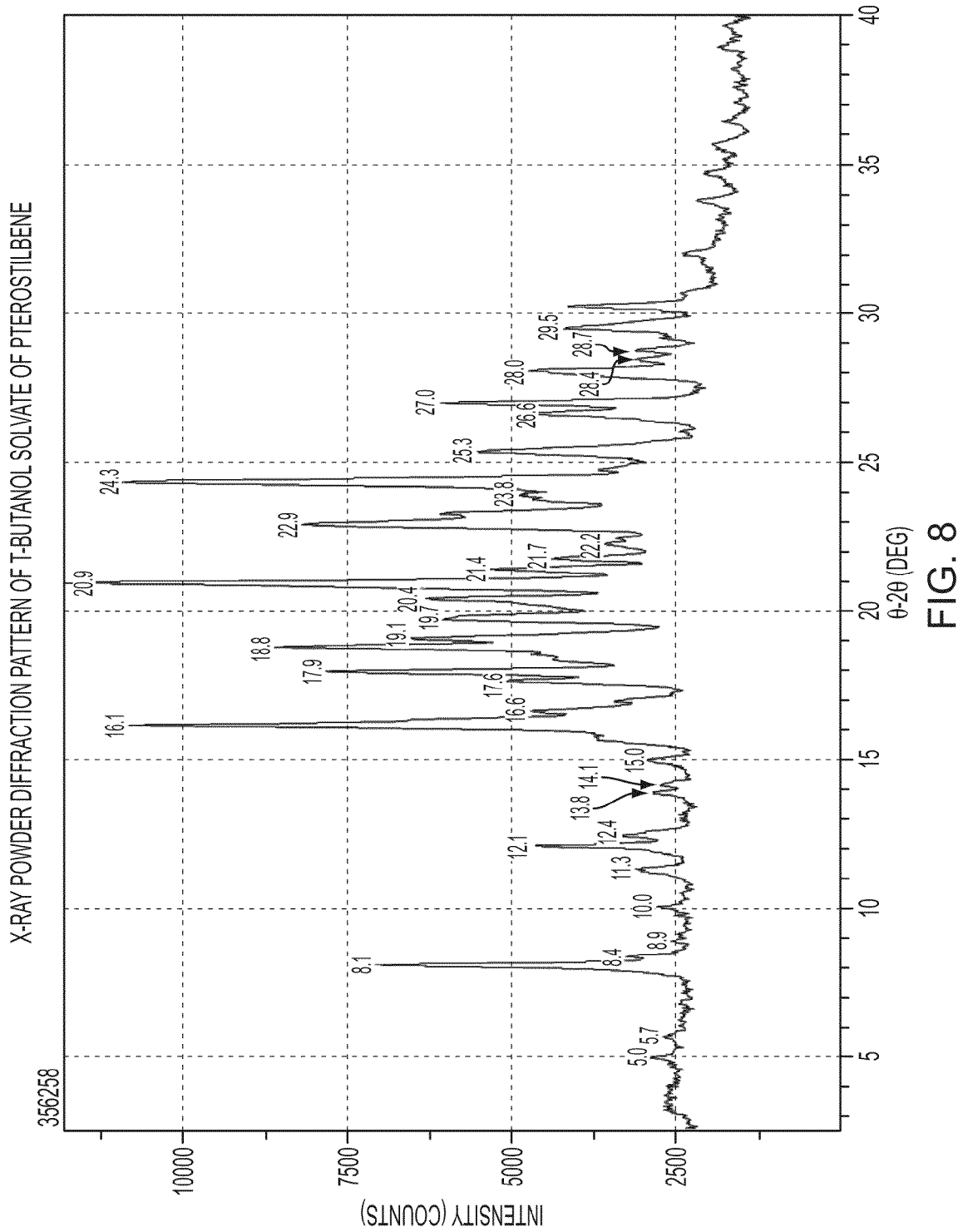
FIG. 8 is an x-ray powder diffraction pattern of the t-butanol solvate of Pterostilbene.

FIG. 8 is the x-ray powder diffraction pattern of the t-butanol solvate of Pterostilbene. The t-butanol solvate can be distinguished from any one of the polymorphs of Pterostilbene due to the presence of t-butanol within the unit cell of the compound. The selection of characteristic peaks of the t-butanol solvate was, therefore, based on using low-angle peaks with sufficient intensity. Thus, one or more of the peaks at about 8.1 and 16.1°2θ can further be used to characterize this form.

Figure 9:
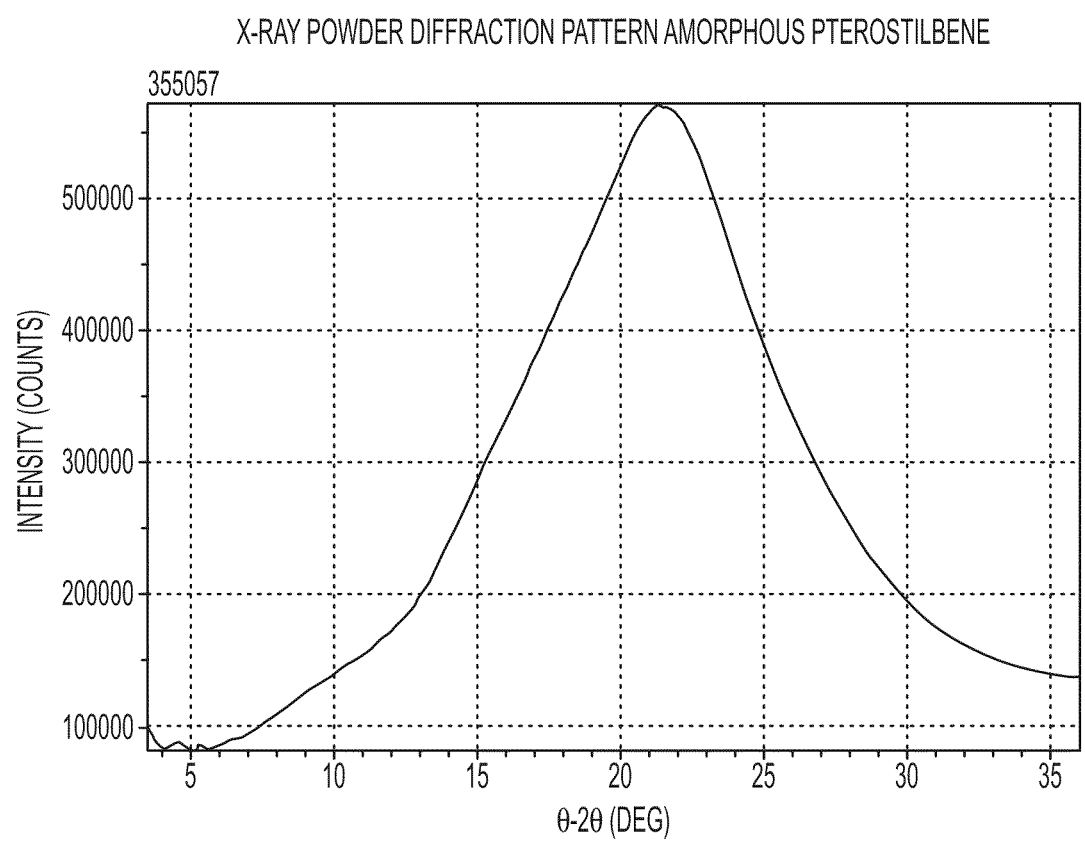
FIG. 9 is an x-ray powder diffraction pattern of x-ray amorphous Pterostilbene.

FIG. 9 is the x-ray diffraction pattern of x-ray amorphous Pterostilbene. By use the term "x-ray amorphous" what is meant is a material whose powder x-ray powder diffraction pattern is consistent with an amorphous "halo" as that term is understood in the art. By inspection, one of ordinary skill in the art would recognize that the pattern in FIG. 9 does represents a material without any significant crystallinity. However, the material may be nanocrystalline or some other disordered solid. The glass transition temperature of amorphous Pterostilbene was experimentally determined (by modulated DSC) to be approximately 4° C. As is often the case with materials exhibiting sub-ambient glass transition temperatures, amorphous Pterostilbene rapidly crystallized under ambient conditions.

Figure 10:
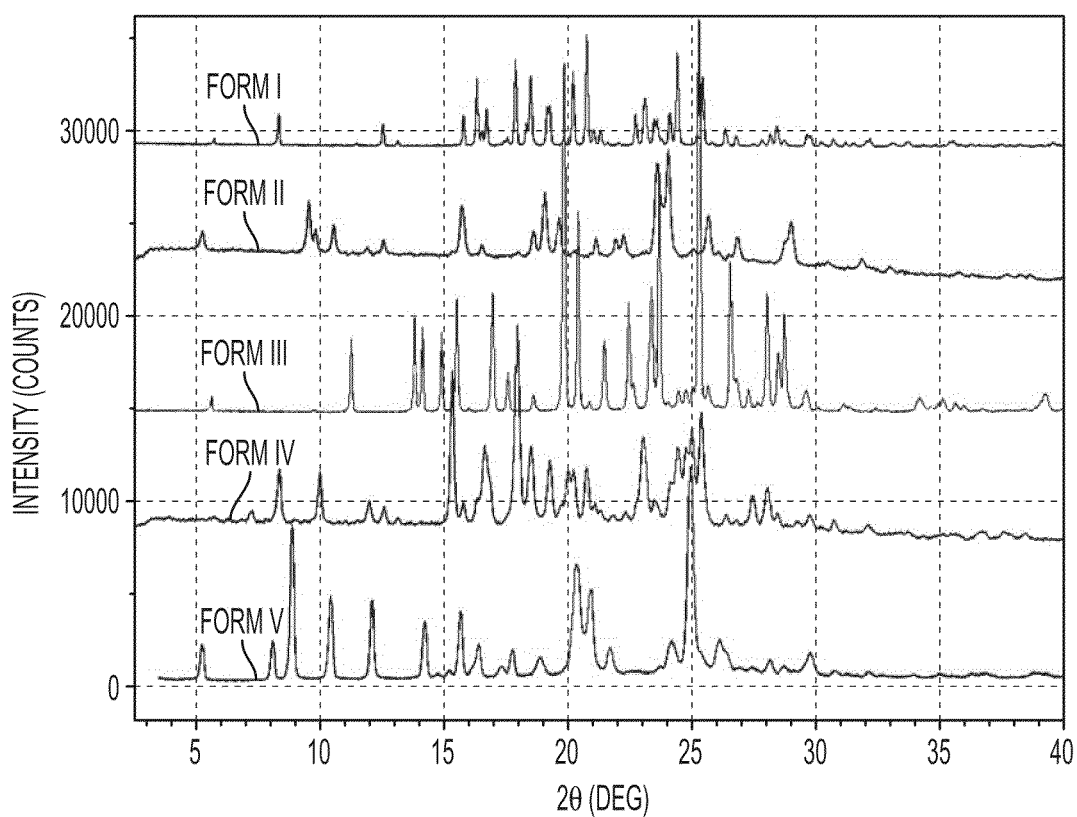
FIG. 10 is a stack plot of x-ray powder diffraction patterns of Forms I-V of Pterostilbene.

In FIG. 10, a stack plot of the x-ray diffraction patterns of Forms I-V of Pterostilbene are presented in one plot to illustrate visually the differences among the forms.

Figure 11:
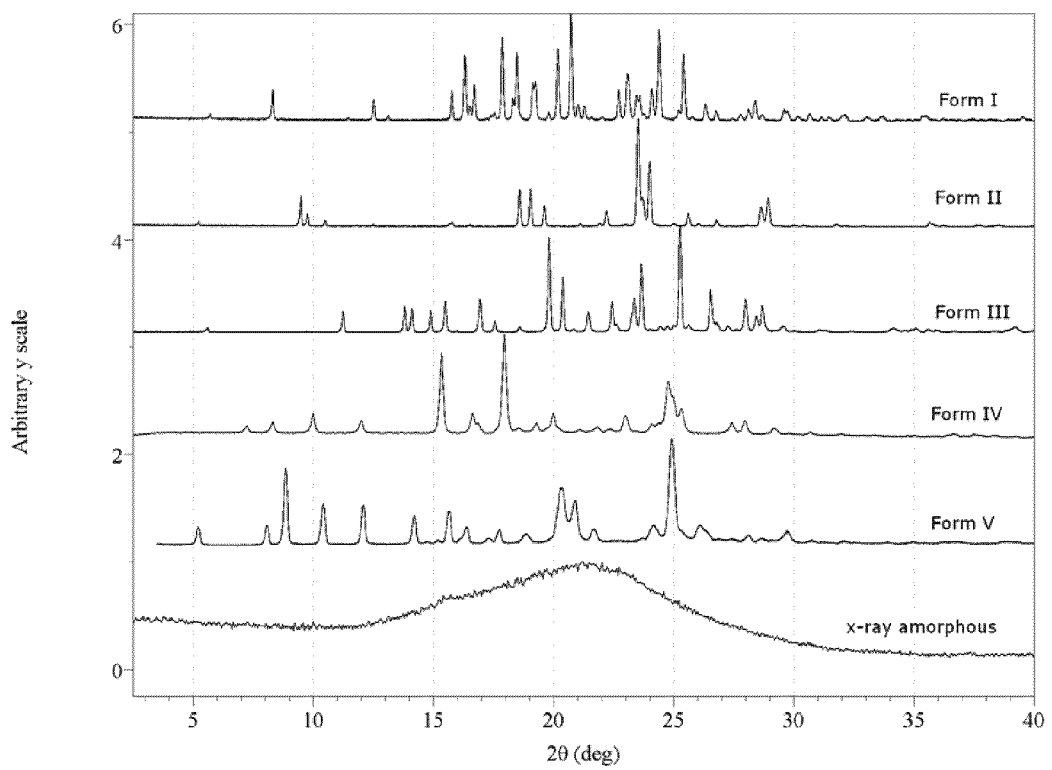
FIG. 11 is a stack plot of experimental x-ray powder diffraction patterns of solid forms of Pterostilbene.

FIG. 11 is a stack plot of experimental x-ray powder diffraction patterns of solid forms of Pterostilbene, including Forms I-V and the amorphous form.

The Raman spectra of Forms I-V of Pterostilbene are presented in FIGS. 12-16. Any of these figures can be used to characterize their respective form of Pterostilbene, however, it is not necessary to use the entire figure to characterize said forms. FIG. 19 is a peak list of the Raman spectra for the polymorphic forms of Pterostilbene.

Figure 12:
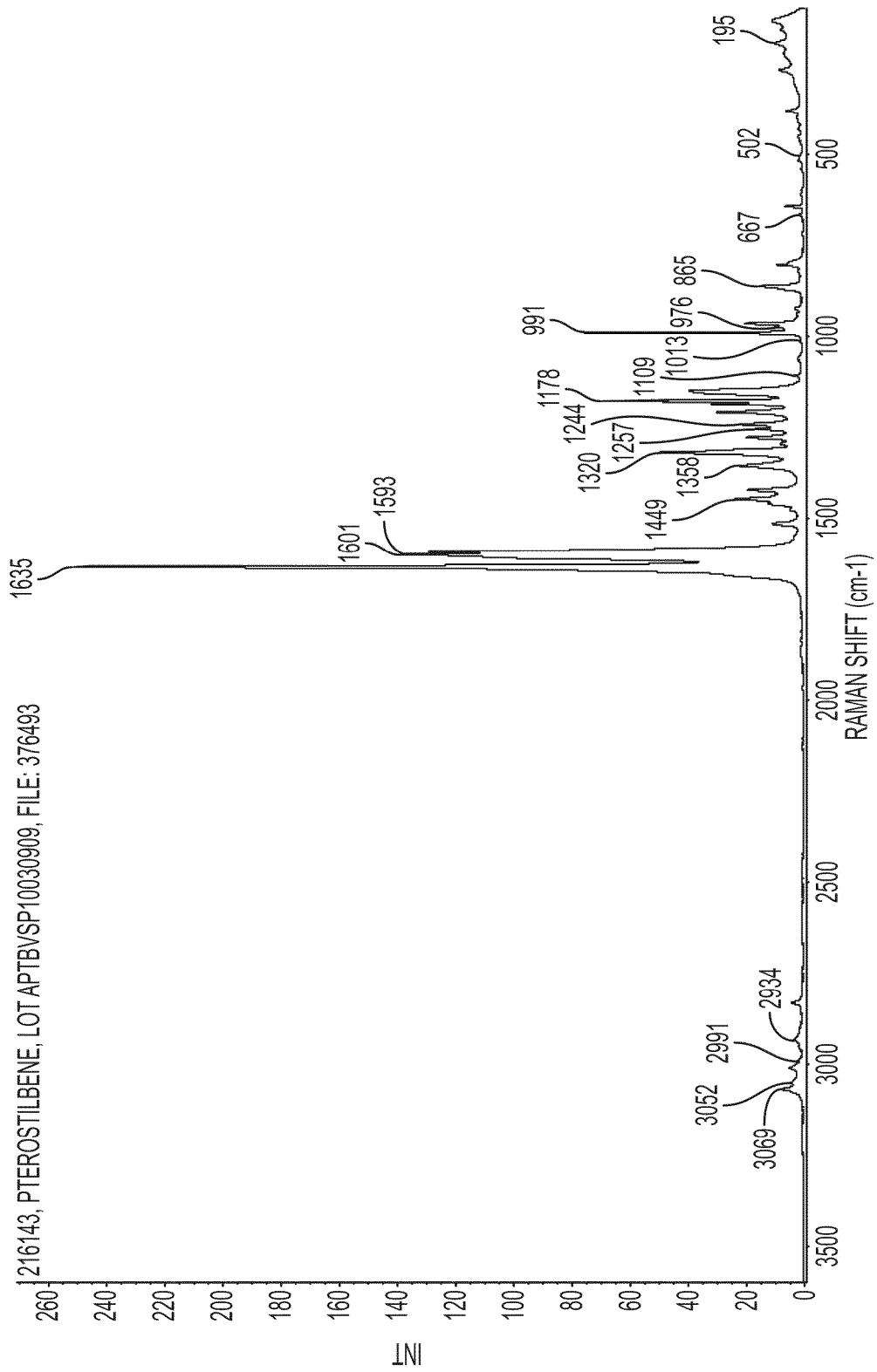
FIG. 12 is a Raman spectrum of Pterostilbene Form I.

FIG. 12 is the Raman spectrum of Pterostilbene Form I. In order to differentiate Form I of Pterostilbene from the other polymorphs of Pterostilbene, the peaks were evaluated and compared to the peaks of the other forms described herein. The peak at about 865 cm$^{-1}$ is not present in Forms II or III. The peak at 1358 cm$^{-1}$ is not present in Form V. The peak at 195 cm$^{-1}$ in Form I is not present in Form IV. Thus, Form I of Pterostilbene can be characterized by Raman peaks at about 195, 865 and 1358 cm$^{-1}$. In addition, Form I can be distinguished by melting point from Form IV. Form IV as prepared was measured to have a melting point of about 76° C. whereas Form I was measured to have a melting point of about 94-96° C. Thus, Form I of Pterostilbene can also be characterized by Raman peaks at about 865 and 1358 cm$^{-1}$ and by a melting point of about 94-96° C. with or without the peak at about 195 cm$^{-1}$.

Other peaks in the Raman spectrum of Form I, such as one or more peaks selected from about 1178, 1320 and 1593 cm$^{-1}$ can further be used to characterize Form I of Pterostilbene.

Figure 13:
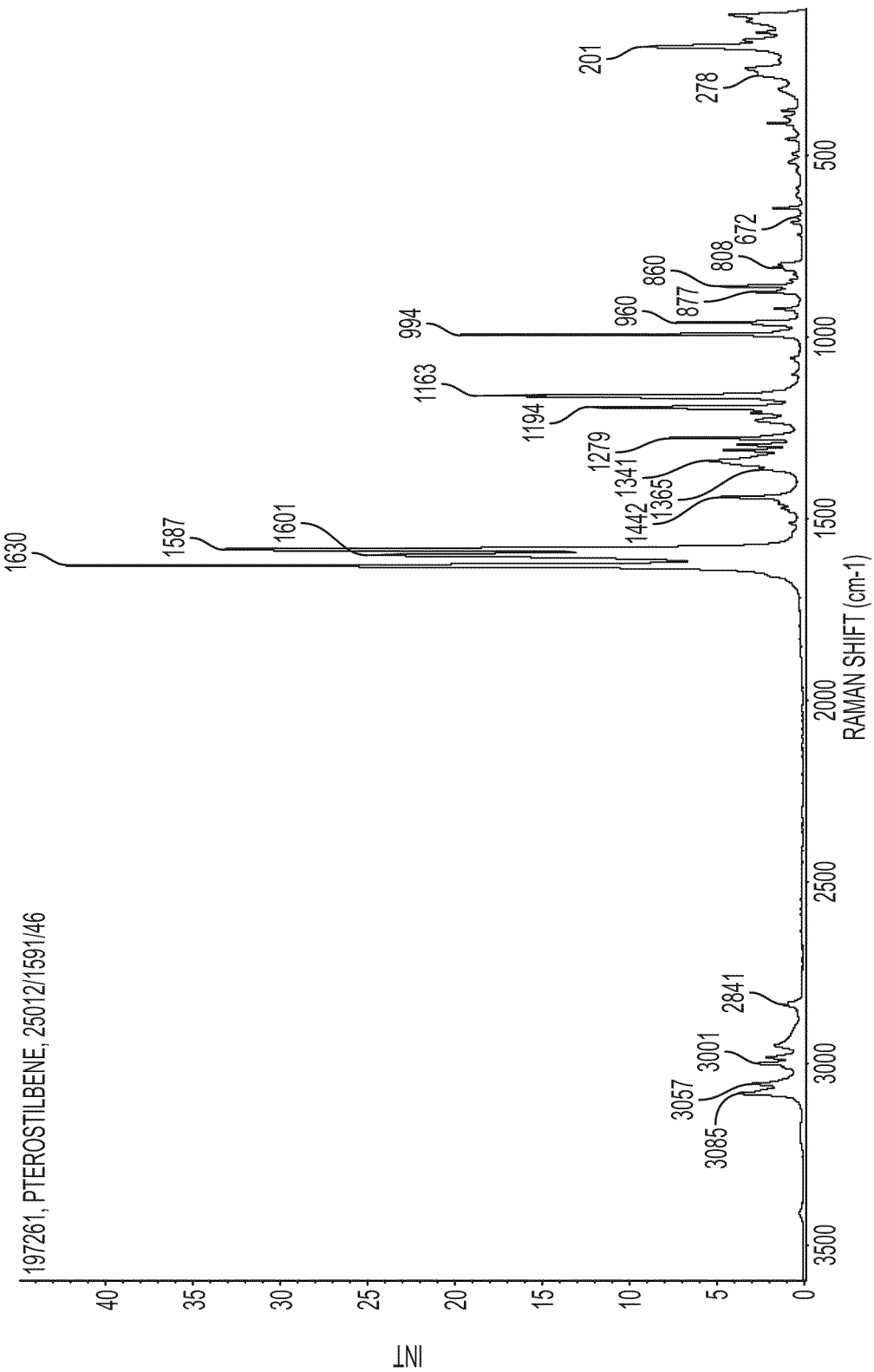
FIG. 13 is a Raman spectrum of Pterostilbene Form II.

FIG. 13 is the Raman spectrum of Form II of Pterostilbene. In order to differentiate Form II of Pterostilbene from the other polymorphs of Pterostilbene, the peaks were evaluated and compared to the peaks of the other forms described herein. The peak at about 960 cm$^{-1}$ is not present in Form I. The peak at about 1587 cm$^{-1}$ is not present in Forms III or V. The peak at about 1442 cm$^{-1}$ is not present in Form IV or Form I. Thus, Form II of Pterostilbene can be characterized by Raman peaks at about 960, 1587, and 1442 cm$^{-1}$.

Other peaks in the Raman spectrum of Form II, such as one or more peaks selected from about 201, 1163, and 1194 cm$^{-1}$ can further be used to characterize Form II of Pterostilbene.

Figure 14:
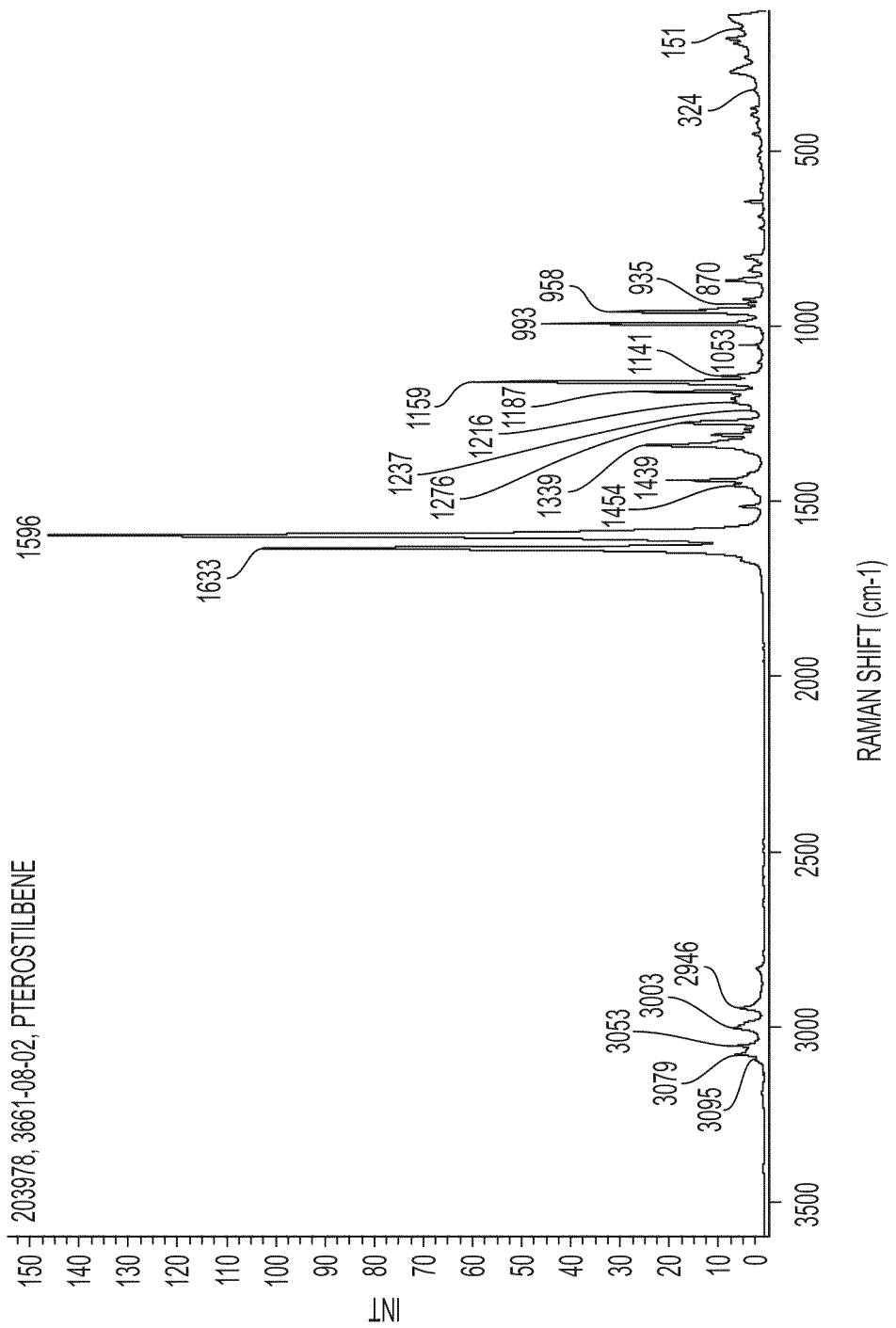
FIG. 14 is a Raman spectrum of Pterostilbene Form III.

FIG. 14 is the Raman spectrum of Form III of Pterostilbene. In order to differentiate Form III of Pterostilbene from the other polymorphs of Pterostilbene, the peaks were evaluated and compared to the peaks of the other forms described herein. The peak at about 958 cm$^{-1}$ is not present in Form I. The peak at about 1187 cm$^{-1}$ is not present in Form II. The peak at about 1439 cm$^{-1}$ is not present in Form IV, Form V or Form I. Thus, Form III of Pterostilbene can be characterized by Raman peaks at about 958, 1187, and 1439 cm$^{-1}$.

Other peaks in the Raman spectrum of Form III, such as one or more peaks selected from about 1339 and 1596 cm$^{-1}$ can further be used to characterize Form III of Pterostilbene.

Figure 15:
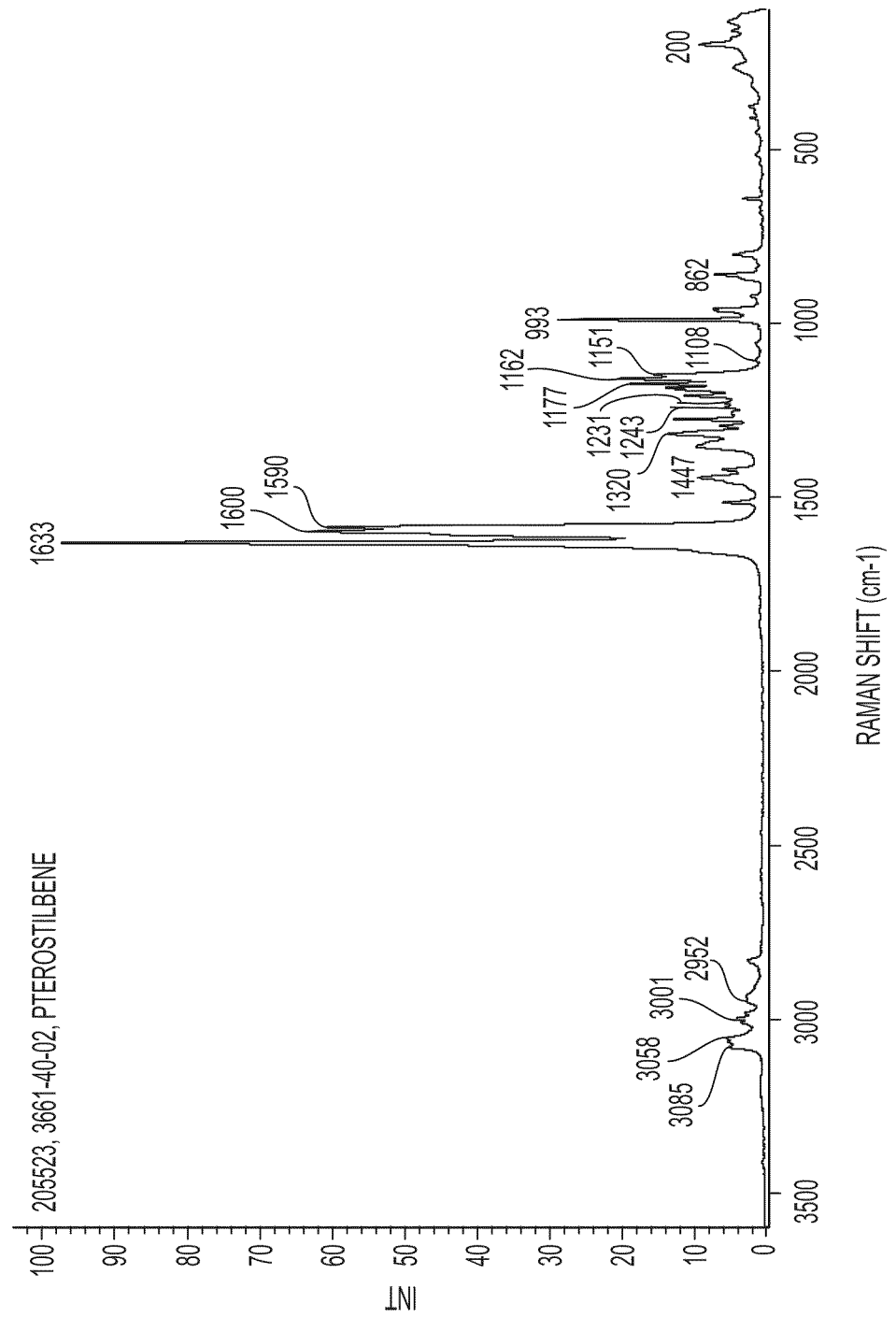
FIG. 15 is a Raman spectrum of Pterostilbene Form IV.

FIG. 15 is the Raman spectrum of Pterostilbene Form IV. In order to differentiate Form IV of Pterostilbene from the other polymorphs of Pterostilbene, the peaks were evaluated and compared to the peaks of the other forms described herein. The peak at about 862 cm$^{-1}$ is not present in Forms III or Form V. The peak at about 1320 cm$^{-1}$ is not present in Form II, Form III, or Form V. The peak at about 200 cm$^{-1}$ is not present in Form I, Form III, or Form V. Thus, the peaks at about 200, 862 and 1320 cm$^{-1}$ characterize Form IV. In addition, Form IV as prepared was measured to have a melting point of about 76° C. whereas Form I was measured to have a melting point of about 94-96° C. Thus, Form IV of Pterostilbene can also be characterized by Raman peaks at about 862 and 1320 cm$^{-1}$ and a melting point of about 76° C. with or without a Raman peak at about 200 cm$^{-1}$.

Other peaks in the Raman spectrum of Form IV, such as one or more peaks selected from about 1231 and 1177 cm$^{-1}$ can further be used to characterize Form IV of Pterostilbene.

Figure 16:
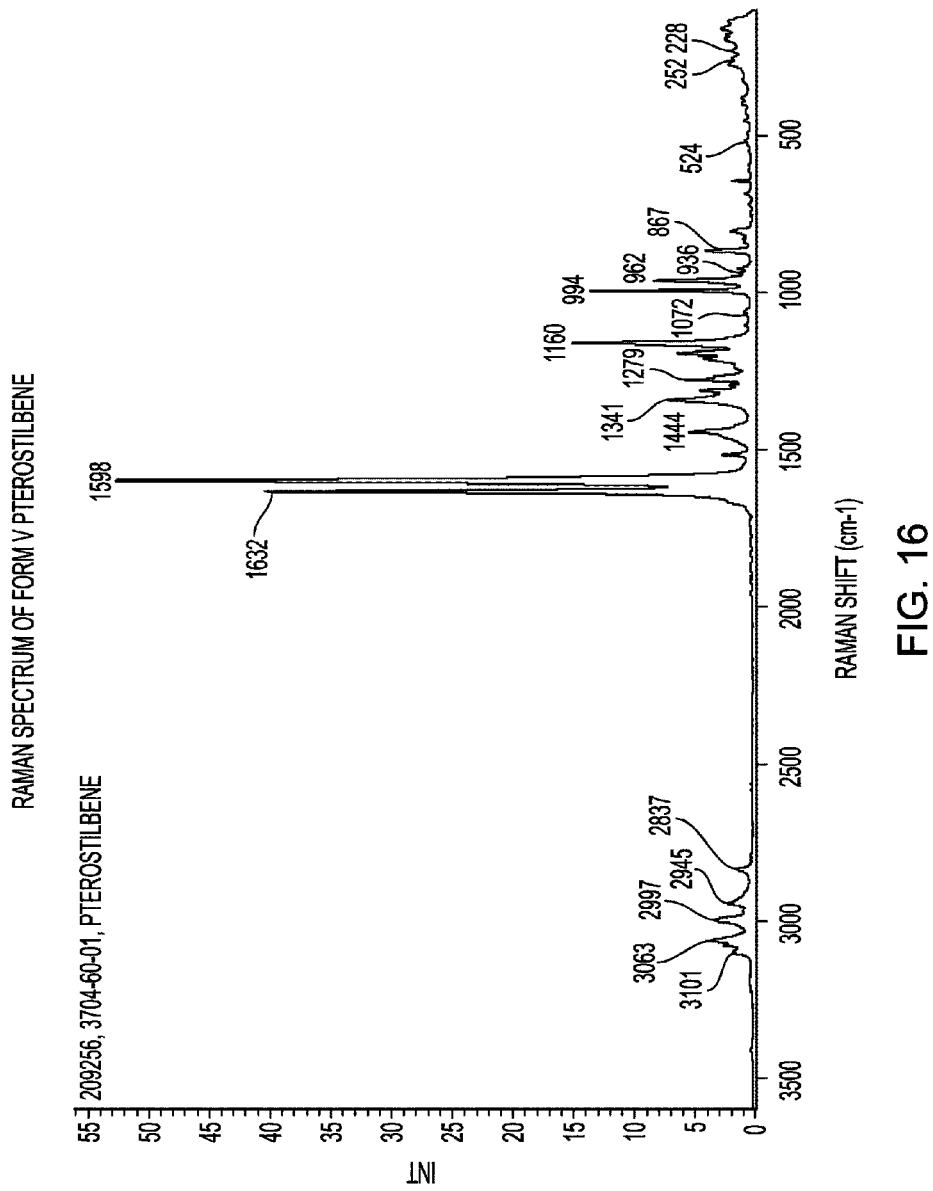
FIG. 16 is a Raman spectrum of Pterostilbene Form V.

FIG. 16 is the Raman spectrum of Pterostilbene Form V. In order to differentiate Form V of Pterostilbene from the other polymorphs of Pterostilbene, the peaks were evaluated and compared to the peaks of the other forms described herein. The peak at about 867 cm$^{-1}$ is not present in Forms II or IV. The peak at about 962 cm$^{-1}$ is not present in Form I. The peak at about 1444 cm$^{-1}$ is not present in Form III, Form I, or Form IV. Thus, Form V of Pterostilbene can be characterized by Raman peaks at about 867, 962, and 1444 cm$^{-1}$.

Other peaks in the Raman spectrum of Form V, such as one or more peaks selected from about 1160 and 1341 cm$^{-1}$ can further be used to characterize Form V of Pterostilbene.

Figure 17:
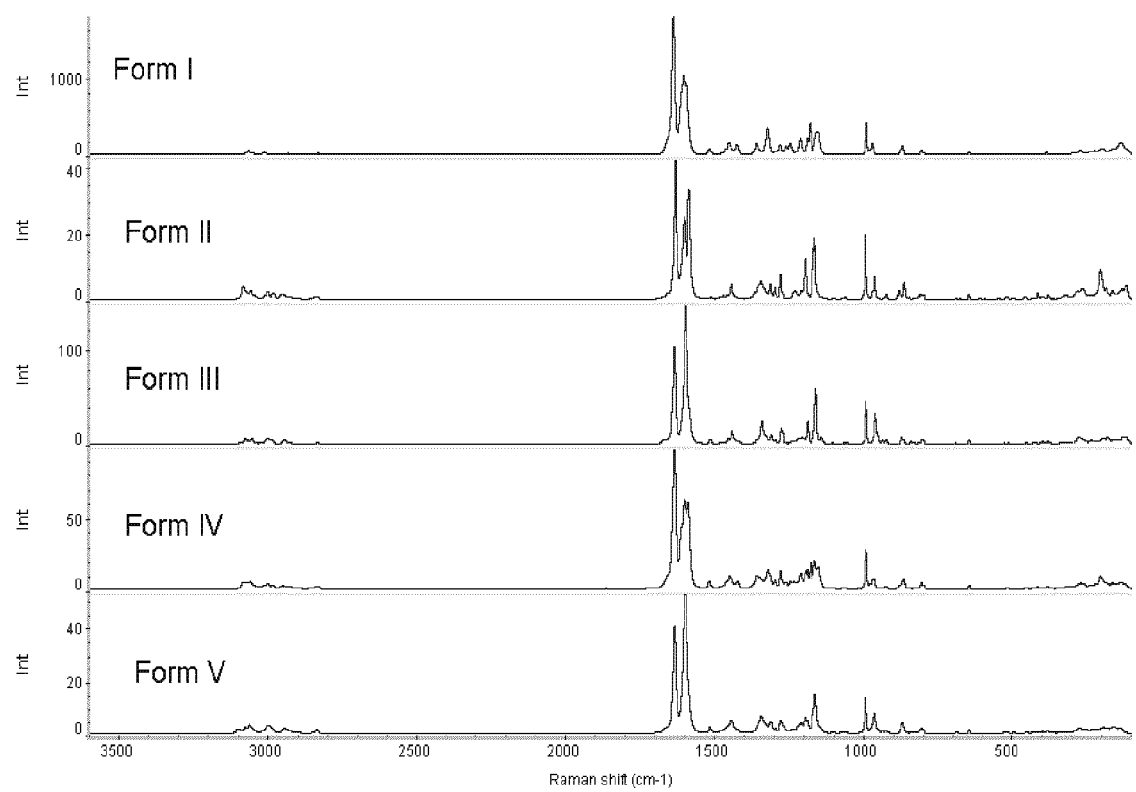
FIG. 17 is a stack plot of Raman spectrum of Pterostilbene Forms I-V.

FIG. 17 is a stack plot of experimental Raman spectrum of Pterostilbene Forms I-V.

Figure 18:
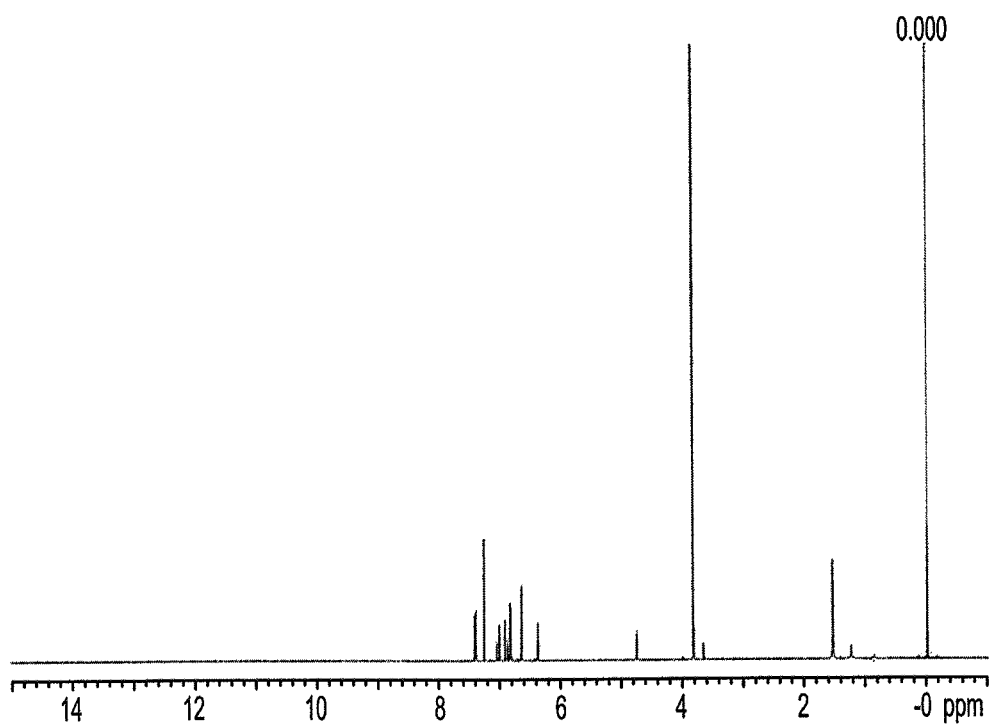
FIG. 18 is 1H NMR spectrum of Pterostilbene.

FIG. 18 is the $^1$H NMR spectrum of Pterostilbene which can be used to verify its chemical structure.

The Raman spectra of the Pterostilbene crystalline forms are dominated by the strong bands at approximately 1630 cm-1 and 1600 cm-1, which are assigned to ν(C=C) of the ethylenic group and ν(C=C) vibrations of the phenyl rings. The Raman spectra of Forms III and V are characterized by a single intense band in this aromatic ring stretching region, in contrast to the two bands observed for Form II, and the three bands of medium intensity for Forms I and IV.

Prominent bands of medium intensity are observed in the Raman spectra at approximately 1160 cm-1 and 990 cm-1, which are assigned to C—H deformation modes of the phenyl rings. The Raman spectra of Forms II and III are characterized by a single intense band in the region near 1160 cm-1, in contrast to the two bands of relatively weaker intensity for Forms IV and V, and the single broad weaker band for Form I. The band near 990 cm-1 displays only slight variability in frequency among the solid state forms of Pterostilbene. The Raman spectra of Forms II-V also display a single weak peak at varying frequency in the region above 3400 cm-1, assigned to the O—H stretch of Pterostilbene. This peak is not observed in the Raman spectrum of Form I.

The polymorphs of Pterostilbene described herein can be characterized by a variety of techniques. Illustrated herein are characterizations done by x-ray powder diffraction, thermal methods such as melting point, and Raman spectroscopy. Those of ordinary skill in the art will recognize that combinations of these techniques can also be used to characterize the polymorphs of Pterostilbene. For example, peaks from both the Raman spectrum and from an x-ray diffraction pattern could be used in combination to characterize a particular polymorph of Pterostilbene following the general principles of identifying distinguishing peaks as disclosed herein.

Figure 20:
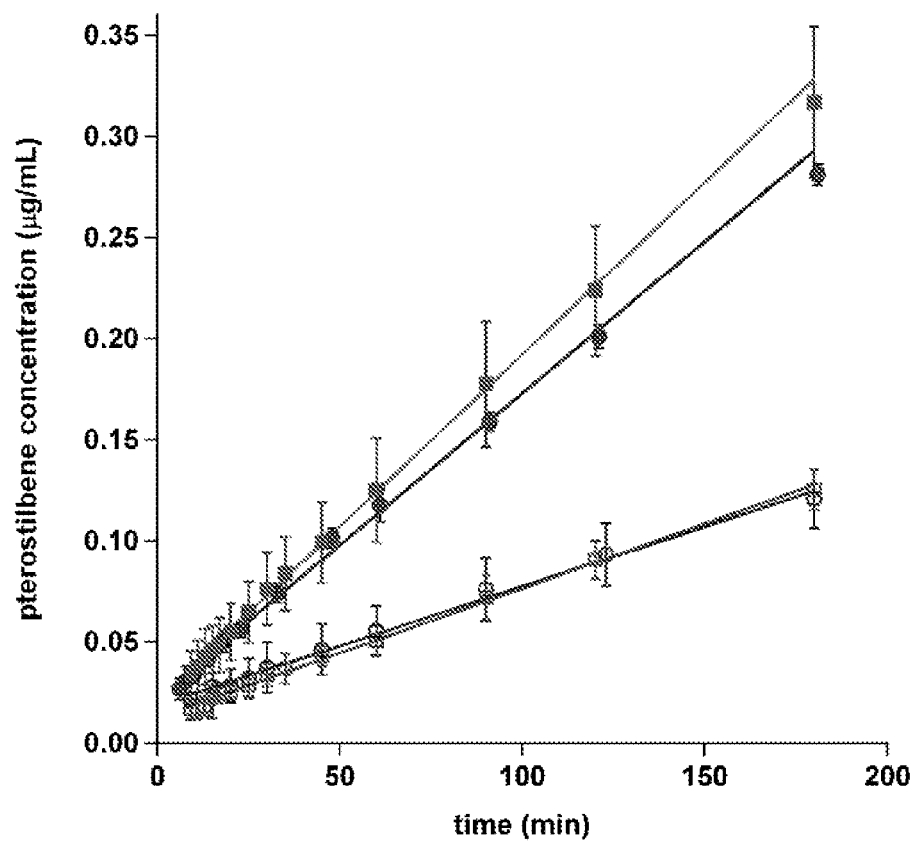
FIG. 20 is a timeline graph of dissolution profiles for Forms I and II of Pterostilbene.

The polymorphs of Pterostilbene described herein can also be characterized by their respective dissolution rates. FIG. 20 shows dissolution profiles of Pterostilbene Form I (circles) and Form II (squares) in water at 25° C. (open symbols) and 37° C. (filled symbols). Table 5 shows the experimental dissolution rates.

TABLE 5

Intrinsic dissolution rates of Form I and Form II in water at 25° C. and 37° C.

| Form | 25° C. (μg/cm$^{-2}$/min) | 37° C. (μg/cm$^{-2}$/min) |
|---|---|---|
| I | 0.83 ± 0.06 | 2.05 ± 0.03 |
| II | 0.90 ± 0.03 | 2.35 ± 0.08 |

In one embodiment of the disclosure, Form I Pterostilbene may be prepared by treating a solution of (2-4-[(E)-2-(3,5-dimethoxyphenyl)-1-ethenyl]phenoxy tetrahydro-2H-pyran) with pyridinium p-toluenesulfonate in a suitable solvent, followed by removing the solvent by vacuum to obtain a solid, purifying the solid, redissolving it in a suitable solvent, and precipitating it to afford Form I Pterostilbene. Embodiments for the preparation of Form I include the preparation of substantially pure Form I.

In an additional embodiment of the disclosure, Pterostilbene form I may be prepared by dissolving solid Pterostilbene of any form in a suitable solvent followed by evaporation of solvent. One such suitable solvent is trifluoroethanol. Embodiments for the preparation of Form I include the preparation of substantially pure Form I.

In another embodiment of the disclosure, Form II may be prepared by recrystallizing Form I Pterostilbene and then dissolving in a suitable solvent and heated followed by cooling to result in Form II.

In yet another embodiment, Form II may be prepared by dissolving solid Pterostilbene of any form in a suitable solvent followed by evaporation of solvent. One such suitable solvent is acetonitrile. Embodiments for the preparation of Form II include the preparation of substantially pure Form II.

In another embodiment of the invention, Form III Pterostilbene may be prepared by dissolving solid Pterostilbene of any form in a suitable solvent followed by evaporation of solvent. One such suitable solvent is methanol. Embodiments for the preparation of Form III include the preparation of substantially pure Form III.

In a further embodiment of the invention, Form IV Pterostilbene may be prepared by dissolving solid Pterostilbene of any form in a suitable solvent followed by slow evaporation of solvent. One such suitable solvent is methanol.

By "slow evaporation" what is meant is evaporation that is limited so that it occurs at a slower rate than by leaving a container open to ambient conditions. Slow evaporation may be accomplished by, for example, covering portions of a container containing the solution to be evaporated. In one embodiment, evaporation conditions are chosen such that for a slow evaporation, evaporation time is greater than about three times the evaporation time than under standard conditions. In a further embodiment, that time is between about three to four times slower than under standard conditions.

In yet another embodiment of the invention, Form V Pterostilbene may be prepared by melting Pterostilbene of any form to form amorphous Pterostilbene and exposing the amorphous pteristilbene to a sufficiently low-humidity environment, such as approximately 10% or less relative humidity, at approximately room temperature to convert the amorphous Pterostilbene into Form V Pterostilbene. The preparation of Form V includes embodiments for the preparation of substantially pure Form V.

In a further embodiment, x-ray amorphous Pterostilbene may be prepared by melting any form of Pterostilbene.

In an additional embodiment of the invention, the t-butanol solvate of Pterostilbene may be prepared by making saturated solutions of Pterostilbene in t-butanol, cooling, and lyophilizing.

By "suitable solvent" what is meant is a solvent suitable for the formation of the particular polymorph or solid form of Pterostilbene of interest. Such solvents are determined empirically. For example, under certain conditions, methanol is a suitable solvent for the preparation of either Form III or Form IV of Pterostilbene whereas under certain conditions acetonitrile is a suitable solvent for the preparation of Form II of Pterostilbene.

Other embodiments of the present disclosure include compositions containing one or more solid forms of Pterostilbene such as pharmaceutical or nutraceutical dosage forms. Such pharmaceutical dosage forms may include one or more excipients, including, without limitation, binders, fillers, lubricants, emulsifiers, suspending agents, sweeteners, flavorings, preservatives, buffers, wetting agents, disintegrants, effervescent agents and other conventional excipients and additives. The compositions of the present disclosure can thus include any one or a combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to humans without causing deleterious side effects or interactions.

Suitable additives may include, but are not limited to, microcrystalline cellulose, lactose, sucrose, fructose, glucose, dextrose, other sugars, di-basic calcium phosphate, calcium sulfate, cellulose, methylcellulose, cellulose derivatives, kaolin, mannitol, lactitol, maltitol, xylitol, sorbitol, other sugar alcohols, dry starch, dextrin, maltodextrin, other polysaccharides, or mixtures thereof.

In one embodiment of the disclosure the solid-form Pterostilbene dosage form is an oral dosage form. Exemplary oral dosage forms for use in the present disclosure include tablets, capsules, powders, solutions, syrups, suspensions and lozenges, which may be prepared by any conventional method of preparing pharmaceutical oral dosage forms. Oral dosage forms, such as tablets, may contain one or more of the conventional, pharmaceutically acceptable additional formulation ingredients, including but not limited to, release modifying agents, glidants, compression aides, disintegrants, effervescent agents, lubricants, binders, diluents, flavors, flavor enhancers, sweeteners and preservatives. These ingredients are selected from a wide variety of excipients known in the pharmaceutical formulation art. Depending on the desired properties of the oral dosage form, any number of ingredients may be selected alone or in combination for their known use in preparing such dosage forms as tablets.

The disclosure also provides methods for delivering the dosage forms to humans. Pterostilbene, an anti-oxidant, is known be beneficial for human health. The dosage forms may be administered using any amount, any form of pharmaceutical composition and any route of administration effective for the treatment. After formulation with an appropriate pharmaceutically acceptable carrier in a desired dosage, as known by those of skill in the art, the pharmaceutical compositions of this disclosure can be administered to humans and other animals orally, rectally, parenterally, intravenously, intracisternally, intravaginally, intraperitoneally, topically (as by powders, ointments, or drops), bucally, as an oral or nasal spray, or the like, depending on the location and severity of the condition being treated. In one embodiment of the disclosure, the method of delivery is with an oral dosage form.

In certain embodiments, solid forms of Pterostilbene may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired effect. It will also be appreciated that dosages smaller than 0.001 mg/kg or greater than 50 mg/kg (for example 50-100 mg/kg) can be administered to a subject.

EXAMPLES

The present invention will now be further explained in the following examples. However, the present invention should not be construed as limited thereby. One of ordinary skill in the art will understand how to vary the exemplified preparations and procedures to obtain the desired results.

Example 1

Synthesis of Pterostilbene

Step-1.1:
To the sodium hydride (1.66 g, 0.0694 mol) suspension in tetrahydrofuran (40 ml) at 0° C. was added diethyl-3,5-dimethoxy benzyl phosphonate (10 g, 0.0347 mol) and resulting dark solution was stirred under nitrogen at room temperature for 30 min. A solution of 4'-O-tetrahydropyranyl benzaldehyde (7.84 g, 0.0381 mol), in tetrahydrofuran (20 ml) was added at 18-20° C. and the mixture stirred at room temperature for about 2-3 hours. After completing the reaction added methanol (10 ml) drop wise at 0-5° C., resulting solution was poured into ice-water and extracted with ethyl acetate (50 ml). Organic layer washed with water (10 ml) and dried over sodium sulfate and removed ethyl acetate under reduced pressure at 40° C. to obtain semi solid and which on treating with methanol given pure solid compound (8.2 g, purity by HPLC 98.4%).

Step-1.2:

To a solution of 3,5-Dimethoxy-4'-O-tetrahydropyranyl stilbene (10 g, 0.0294 mol) in methanol (50 ml) at RT was added PPTS (0.369 g, 0.264 mol) under stirring and contents were heated under reflux for 1 h. After completion of the reaction, solvent was distilled off under reduced pressure to get residue. The residue was dissolved in ethyl acetate and treated with 5% HCl, then with 5% NaHCO$_3$, finally with water and separated organic phase. Removal of solvent in vacuo from the organic phase yielded the crude Pterostilbene, which was purified further by washing with 10% ethyl acetate and hexanes (10 ml) to get pure Pterostilbene (5.5-6.7 g, purity by HPLC 99%).

Example 2

Synthesis of Resveratrol

Step-2.1:

To the sodium hydride (1.66 g, 0.0694 mol) suspension in tetrahydrofuran (40 ml) at 0° C. was added diethyl-3,5-dimethoxy benzyl phosphonate (10 g, 0.0347 mol) and resulting dark solution was stirred under nitrogen at room temperature for 30 min. A solution of 4'-O-tetrahydropyranyl benzaldehyde (7.84 g, 0.0381 mol) in tetrahydrofuran (20 ml) was added at 18-20° C. and the mixture stirred at room temperature for about 2-3 hours. After completing the reaction added methanol (10 ml) drop wise at 0-5° C., resulting solution was poured into ice-water and extracted with ethyl acetate (50 ml). Organic layer washed with water (10 ml) and dried over sodium sulfate and removed ethyl acetate under reduced pressure at 40° C. to obtain semi solid and which on treating with methanol given pure solid compound (8.2 g, purity by HPLC 98.4%).

Step-2.2:

To a solution of N,N-Dimethylaniline (32 g, 0.264 mol) in 500 ml RB flask at RT, was added slowly Aluminum chloride (35.2 g, 0.264 mol) under stirring, over a period of 15 min. The temperature of the reaction rose to 70° C. during the addition and toluene (50 ml) was added after 30 min and heated to 80° C. for another 30 min. To the reaction mixture at 80° C., was added drop wise, 3,5-Dimethoxy-4'-O-tetrahydropyranylstilbene (10 g, 0.0294 mol) in toluene (50 ml) under stirring and the contents were heated under reflux for further 3 h. After completion of the reaction, the contents were cooled to room temperature and the solvent was decanted. The residue was treated with dil. HCl (30 ml) and extracted the product into ethyl acetate (2×50 ml), solvent was distilled off under reduced pressure to obtain crude Resveratrol which was purified further by washing with dichloromethane (10 ml) to get pure Resveratrol (4.7-6.0 gm, purity by HPLC 99%).

Experimental Procedures

X-ray powder diffraction (XRPD) patterns on Form IV and the t-butanol solvate were collected using an Inel XRG-3000 diffractometer (Artenay, France) equipped with a curved position sensitive detector with a 2θ range of 120° and operated in transmission mode. An incident beam of Cu Kα radiation (40 kV, 30 mA) was used to collect data in real time at a resolution of 0.03°2θ. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition. The monochromator slit was set at 5 mm by 160 μm, and the samples were analyzed for 5 minutes.

Additional XRPD patterns were collected using two PANalytical X'Pert Pro diffractometers (Almelo, The Netherlands) configured in reflection and transmission geometries, respectively. In reflection mode, Form V was analyzed using (Bragg-Brentano geometry), an incident beam of Cu Kα radiation (45 kV, 40 mA) was produced using a ceramic tube with a long, fine-focus source and a nickel filter. A reflection stage and a manually operated spinner were used. The specimen was prepared as a thin, circular layer centered on a silicon zero-background substrate. The data were collected from 3.5-40.0°2θ at a resolution of 0.008°2θ for approximately 30 min. An Anton Paar (Ashland, Va.) TCU 100 Temperature Control Unit and a VTI (Hialeah, Fla.) RH-200 Relative Humidity Generator were used for temperature and humidity-controlled experiments. In transmission mode, Forms I, II, and III and the amorphous form were analyzed using an incident beam of Cu Kα radiation (45 kV, 40 mA) was produced using an Optix long, fine-focus source. An elliptically graded multilayer mirror was used to focus the Cu Kα X-rays of the source through the specimen and onto the detector. The specimen was sandwiched between 3 μm thick Etnom® films and rotated to optimize orientation statistics. In some cases, a beam-stop and a helium atmosphere were used to minimize the background generated by air scattering and produce data suitable for indexing. The data were collected from 1.0-40.0°2θ at a resolution of 0.017°2θ for 12-32 min.

For both PANalytical geometries, anti-scatter slits were used to minimize the background generated by air scattering and soller slits were used for the incident and diffracted beams to minimize axial divergence (⅛° and ¼°, respectively, for reflection geometry and ½° and ¼°, respectively for transmission geometry). Diffraction patterns were collected using a scanning position-sensitive detector (X'Celerator) located 240 mm from the specimen. PANalytical XRPD data were collected and analyzed using X'Pert Pro Data Collector software (v. 2.2b). Prior to the analysis, a silicon specimen (NIST SRM 640c) was analyzed to verify the Si 111 peak position.

Peak positions are dependent upon x-ray wavelength according to Bragg's law. Instruments utilizing different wavelengths of incident x-ray radiation will result in different °2θ peaks. However given a peak with one wavelength, and by using Bragg's law, one of ordinary skill in the art will readily be able to calculate the appropriate peak in °2θ for another wavelength. Those of ordinary skill in the art will recognize that diffraction angle may also be calculated in d-space also using Bragg's law. Thus, all diffraction peaks provided herein have equivalent d-spacings which can be used to characterize the forms. D-spacings are not dependent upon the wavelength of the incident x-ray. All diffraction peaks reported herein used Cu—K$_\alpha$ radiation.

Most commercial x-ray diffractometers use Cu—K$_\alpha$ radiation. Some commercially available x-ray diffractometers use non-copper sources such as molybdenum, which have different wavelengths than those used in copper. One of ordinary skill in the art can readily calculate the corresponding peak from a molybdenum or other non-copper source in °2θ for a peak reported herein using Cu—K$_\alpha$ radiation.

Differential Scanning Calorimetry (DSC) analyses were performed using a TA Instruments (New Castle, Del.) Q2000 differential scanning calorimeter, equipped with a refrigerated cooling system (RCS). Temperature calibration was performed using NIST traceable indium metal. The sample was placed into an aluminum DSC pan, and the weight was accurately recorded. The pan was covered with a lid perforated with a laser pinhole, and the lid was hermetically sealed. A weighed, crimped aluminum pan was placed on the reference side of the cell. The sample cell was equilibrated at sub-ambient temperature and heated under a nitrogen purge at a rate of 10° C./minute. Higher and lower heating rates were also investigated (from 1 to 300° C./min). Alternatively, data were obtained using a modulation amplitude of +/−0.8° C. and a 60 second period with an underlying heating rate of 2° C./min from −50 to 150° C. The reported glass transition temperatures are obtained from the inflection of the step change in the reversible heat flow versus temperature curve.

Thermogravimetric (TG) analyses were performed using a TA Instruments Q5000 IR thermogravimetric analyzer. Temperature calibration was performed using nickel and Alumel. Each sample was placed in an aluminum pan. The pan was hermetically sealed with a lid that was opened using a punching mechanism just before being inserted into the TG furnace. The furnace was heated under nitrogen at a rate of 10° C./minute.

Raman spectra were acquired on a Thermo Nicolet (Waltham, Mass.) FT-Raman 960 spectrometer equipped with a germanium (Ge) or indium gallium arsenide (InGaAs) detector. Additional Raman spectra were acquired on a Nexus 670 FT-Raman accessory module interfaced to a Nexus 670 FT-IR spectrophotometer (Thermo Nicolet) equipped with an indium gallium arsenide (InGaAs) detector. Wavelength verification was performed using sulfur and cyclohexane. Each sample was prepared for analysis by placing the sample into a glass tube and positioning the tube in a gold-coated tube holder or placing the sample into a pellet holder. Approximately 0.3-0.5 W of Nd:YVO4 laser power (1064 nm excitation wavelength) was used to irradiate the sample. Each spectrum represents 256 co-added scans collected at a spectral resolution of 4 cm$^{-1}$.

The solution nuclear magnetic resonance ($^1$H NMR) spectra were acquired with a Varian (Palo Alto, Calif.) UNITYI-NOVA-400 spectrometer. The spectra were acquired at ambient temperature at a H Larmor frequency of 399.8041924 MHz. The samples were dissolved in CDCl$_3$ and each spectrum was acquired with a $^1$H pulse width of 7.9 μs, a 2.500 second acquisition time, a 5.000 second delay between scans, a spectral width of 6400.0 Hz with 32K data points, and 40 co-added scans. The free induction decay (FID) was processed with 131K points with an exponential line-broadening factor of 0.2 Hz to improve the signal-to-noise ratio. The spectra were referenced to tetramethylsilane (0 ppm), which was present in the NMR solutions as an internal standard.

Water vapor adsorption/desorption (WVS) data were collected on a VTI SGA-100 Vapor Sorption Analyzer. NaCl and PVP were used as calibration standards. Samples were not dried prior to analysis. Adsorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours if the weight criterion was not met. Data were not corrected for the initial moisture content of the samples.

Hot stage microscopy (HSM) was performed using a Linkam (Tadworth, United Kingdom) FTIR 600 hot stage with a TMS93 controller on a Leica DM LP microscope equipped with a SPOT Insight™ color digital camera. Images were acquired using SPOT Advanced software (v. 4.5.9), build date Jun. 9, 2005. Temperature calibrations were performed using USP melting point standards. Samples were placed on a cover glass, and a second cover glass was placed on top of the sample. As the stage was heated, each sample was visually observed using a 20×0.40 N.A. long working distance objective with crossed polarizers and a first order red compensator.

UV-VIS spectrophotometry: samples were analyzed using a SpectraMax M2 Microplate Reader. Wavelength calibration and photometric accuracy was performed using the Spectra-Max Pro 5 software as an internal calibration of the instrument. The instrument was blanked with an empty quartz glass plate. Samples were analyzed in the UV range at ambient temperature in the wells of a 96-well quartz plate. The absorbance spectra of water was collected and subtracted from the spectra of the drug solutions to calculate concentrations. Samples were performed in duplicate and absorbance data was averaged. The standard curve was determined based on absorbance at 310 nm.

Two laboratory lots and one commercial lot of Pterostilbene were obtained from Aptuit Laurus (Hyderabad, India) and used as received. Solvents and reagents were obtained from various commercial suppliers and used as received.

Example 3

Screens for Pterostilbene Solid Forms

Several types of high-throughput and manual crystallization experiments were conducted on Forms I and II of Pterostilbene using many different types of solvents. The solvents were chosen to span a wide range of polarities, functional groups, hydrogen bonding potentials, and the like. In addition, various solvent mixtures were utilized. Crystallization techniques included slow evaporation, fast evaporation, slow cool, crash cool, crash precipitation, ambient and elevated temperature slurrying, and sonication. Five crystalline polymorphs, x-ray amorphous material and a t-butanol solvate of Pterostilbene were identified during the screen. The crystallization and synthetic methods listed for the various forms below were also used to prepare the forms.

Example 4

Synthetic Preparation of Pterostilbene Form I

To a solution of (2-4-[(E)-2-(3,5-dimethoxyphenyl)-1-ethenyl]phenoxy tetra hydro-2H-pyran) (50 g, 0.15 mol, 1 eq) in methanol (250 ml), pyridinium p-toluenesulfonate (7.5 g, 0.03 mol, 0.2 eq) was added at room temperature, and the reaction mass was refluxed for 2 h. After completing the reaction, methanol was removed in vacuo to obtain a residue. The residue was diluted in ethyl acetate, washed with 5% HCl, water, 5% NaHCO$_3$ followed by water. Evaporation of ethyl acetate resulted in a semi solid, which was dissolved in ethyl acetate (25 mL) and product was precipitated by adding slowly hexane (250 mL) at 25-30° C. and filtered, washed the wet cake with hexane (50 mL) to afford pure product (Yield 26.3 g, 70%) and HPLC purity: 99.3%.

Example 5

Preparation of Pterostilbene Form I

Pterostilbene (50 mg, 0.2 mmol) was dissolved in 5 mL of trifluoroethanol. The solution was filtered (0.2 μm) into an open evaporating dish under ambient conditions and allowed to evaporate to dryness.

Example 6

Preparation of Pterostilbene Form II

Another lot was prepared by the procedure in Example 4 which was obtained in 97% purity, and was recrystallized (repeatedly for 3 times), as follows. The Pterostilbene (33 g) obtained from the Example 4 procedure was dissolved in 165 mL (5 vol) of dichloromethane, heptanes mixture (3:2 ratio; 99 mL:66 mL respectively) and warmed to 4° C. to become a clear solution. The reaction mass was slowly cooled to 10° C. and maintained at this temperature for 1 h and filtered, resulted in the compound (Yield 19 g, 57.5%) having HPLC purity: 99.96%.

Example 7

Preparation of Pterostilbene Form II

Pterostilbene Form I (50 mg, 0.2 mmol) was dissolved in 1 mL of acetonitrile. The solution was filtered (0.2 μm) into an open evaporating dish under ambient conditions and allowed to evaporate to dryness.

Example 8

Preparation of Pterostilbene Form III

Pterostilbene Form I (50 mg, 0.2 mmol) was dissolved in 1 mL of methanol. The solution was filtered (0.2 μm) into an open evaporating dish under ambient conditions and allowed to evaporate to dryness.

Example 9

Preparation of Pterostilbene Form IV

Pterostilbene Form I (50 mg, 0.2 mmol) was dissolved in 1 mL methanol. The solution was filtered (0.2 μm) into an evaporating dish under ambient conditions. The solvent evaporation rate was restricted to a slow evaporation and the sample was allowed to evaporate to dryness.

Example 10

Preparation of Pterostilbene Form V

Pterostilbene Form I (50 mg, 0.2 mmol) was placed into an XRPD Ni-coated Cu well holder and carefully melted using a Kofler hot bench. The melted material was determined to be amorphous by x-ray powder diffraction. The sample was immediately placed into a low (~10%) relative humidity environment at 20° C. The sample was continuously monitored by XRPD until the amorphous material had crystallized (~36 hours).

Example 11

Preparation of X-Ray Amorphous Pterostilbene

X-ray amorphous material was generated by melting crystalline Pterostilbene (Form I) directly into a thin-polymer (Etnom®) film sandwich and allowing the sample to solidify at ambient conditions

Example 12

Preparation of T-Butanol Solvate of Pterostilbene

Saturated solutions of Pterostilbene in t-butanol were prepared. The samples were filtered (nylon, 0.2 μm), drop wise, into vials submerged in a dry ice/acetone bath and then placed on a commercial freeze dryer equipped with a rotary vane mechanical vacuum pump and lyophilized.

Example 13

Slurry Interconversion Experiments

Saturated solutions of Pterostilbene were prepared at ambient temperature in toluene. The solutions were filtered and seeds of each form were added. The samples were agitated for days and the solids recovered by vacuum filtration. The solids were collected and allowed to dry under ambient conditions. The results are given in Table 1.

Example 14

Single Crystal Analysis of Form II

Single crystals of Pterostilbene Form II, suitable for single-crystal x-ray diffraction were obtained from crystallizing a 1:2 stoichiometric ratio of Pterostilbene to isonicotinamide by dissolving both components in ethanol and placing the solution in a larger vial containing water (antisolvent) for three days, resulting in crystals of Pterostilbene Form II. Data were collected on a Bruker SMART APEX II using MoKα radiation. Data were collected using APEXII software (APEXII v. 2009.11-0, © 2005-2009, Bruker Analytical X-ray Systems, Madison, Wis.). Initial cell constants were found by small widely separated "matrix" runs. Data collection strategies were determined using COSMO. Scan speed and scan width were chosen based on scattering power and peak rocking curves. Temperature control was provided with an Oxford Croystream low-temperature device. The crystal structure is illustrated in FIG. 4. Table 3 lists data parameters for the crystal structure.

Unit cell constants and orientation matrix were improved by least-squares refinement of reflections thresholded from the entire dataset. Integration was performed with SAINT (SAINT v7.68A, © 1997-2009, Bruker Analytical X-ray Systems, Madison, Wis.) using this improved unit cell as a starting point. Precise unit cell constants were calculated in SAINT from the final merged dataset. Lorenz and polarization corrections were applied. An absorption correction was not applied (μ*d<0.03).

Data were reduced with SHELXTL (SHELXTL v. 2008/4, © 2008, Bruker Analytical X-ray Systems, Madison, Wis.). The structure was solved by direct methods without incident. The coordinates of the H21 —OH hydrogen was allowed to refine; all other hydrogens were placed in idealized positions and were allowed to ride. All non-hydrogen atoms were assigned anisotropic thermal parameters, which were allowed to refine.

Example 15

Indexing of Forms I, II, III, and V

The laboratory XRPD patterns of Pterostilbene Forms I and II were indexed using DASH software, while Forms III and V were indexed using proprietary software. The indexed solutions were verified and illustrated using CheckCell. Successful indexing of these patterns indicated that the samples were composed primarily of a single crystalline phase. Space groups consistent with the assigned extinction symbols, unit cell parameters, and derived quantities are tabulated in Table 2. The indexing solution for Form II is consistent with the experimental single crystal structure solution. Attempts to index Form IV were unsuccessful, likely due to insufficient data quality which may be a result of additional forms of Pterostilbene in the Form IV material as prepared.

Example 16

Thermodynamic Stability of Pterostilbene

Thermodynamic stability relationships of various forms of Pterostilbene were studied by calculating the heat of fusion for each form (from DSC data, see table 4) and through slurry interconversion experiments in toluene. Heat of fusion (ΔH) for Form I was determined (from 10° C./min DSC data) to be approximately 100 J/g or 25.6 kJ/mol. Additional DSC analyses (at 50° C./min) resulted in ΔH values of 106, 102 and 101 J/g, averaging to 103 J/g or 26.4 kJ/mol. Heat of fusion for Form II was determined (from 10° C./min DSC data) to be approximately 92 J/g or 23.6 kJ/mol. Additional DSC analyses (at 50° C./min) resulted in ΔH values of 100, 91 and 92 J/g, averaging to 94 J/g or 24.2 kJ/mol. Heat of fusion for Form III was estimated (from 50° C./min DSC data) to be approximately 75 J/g or 19.2 kJ/mol.

Example 17

Stress Conditions

Stress conditions were employed to evaluate the stability of Pterostilbene Form II. Ambient (air, but not light) exposure left the material structurally unchanged after 70 days and chemically unchanged after 34 days. Moderate humidity stress at ambient and elevated temperatures did not result in deliquescence. Heating at 80° C. for 3 days resulted in conversion to Form I. Organic vapor stress left the material structurally unchanged. Ambient and elevated temperature water slurry experiments starting with Form II material were set up in an effort to produce a hydrate of Pterostilbene. No hydrate was observed and the resulting material was Form II at ambient temperature and Form I at elevated temperature.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

We claim:

1. A compound of formula 1

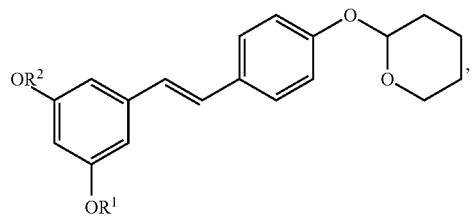

Formula 1 wherein $R^1$ and $R^2$ independently represent hydrogen, lower alkyl or aralkyl.

2. A process for the preparation of the compound of formula 1, comprising the step of condensing 3,5-Dialkylbenzyl phosphonates with 4'-O-tetrahydropyranyl benzaldehyde in presence of a base.

3. The process as claimed in claim 2, wherein the base is sodium hydride.

4. A process for the preparation of stilbene of formula 2,

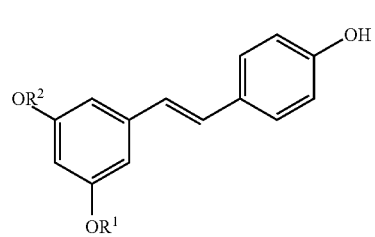

Formula 2 wherein $R^1$ and $R^2$ independently represent hydrogen, lower alkyl or aralkyl, comprising the steps of:
condensing 4'-O-tetrahydropyranyl benzaldehyde with a compound of formula 3

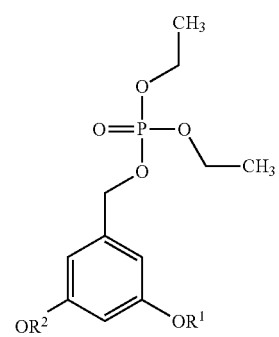

Formula 3 to obtain a compound of formula 1

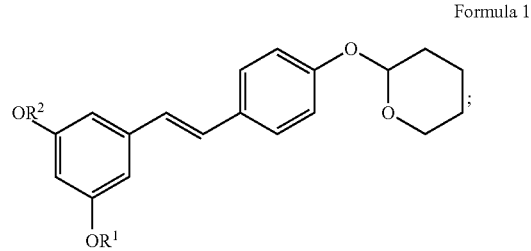

Formula 1 and
deprotecting the compound of formula 1 to obtain the stilbene of formula 2.

5. The process as claimed in claim 4, wherein each of R1 and R2 is methyl, and the stilbene is Pterostilbene.

6. The process as claimed in claim 4, wherein each of R1 and R2 is hydrogen, and the stilbene is resveratrol.

7. Form I Pterostilbene having x-ray powder diffraction peaks, when measured with Cu—Kα radiation, at about 16.7 and 8.3°2θ, and a melting point of about 94-96° C.

8. Form II Pterostilbene having x-ray powder diffraction peaks, when measured with Cu—Kα radiation, at about 5.3, 9.6, and 10.5°2θ.

9. Form III Pterostilbene having x-ray powder diffraction peaks, when measured with Cu—Kα radiation, at about 11.3, 13.8, 14.1, 14.9, and 15.5°2θ.

10. Form IV Pterostilbene having x-ray powder diffraction peaks, when measured with Cu—Kα radiation, at about 8.4, 10.0, 12.0 and 15.3°2θ.

11. Form V Pterostilbene having x-ray powder diffraction peaks, when measured with Cu—K$_\alpha$ radiation, at about 5.2, 8.1, 8.9, 10.4, 12.1, or 14.2°2θ.

12. X-ray amorphous Pterostilbene having substantially the same x-ray powder diffraction pattern of FIG. 9.

13. Pterostilbene Form I of claim 7, further having one or more x-ray powder diffraction peaks at about 12.5 or 15.8°2θ.

14. Pterostilbene Form I of claim 7, having substantially the same x-ray powder diffraction pattern of FIG. 2 when measured with Cu—K$_\alpha$ radiation.

15. Pterostilbene of Form I of claim 7, having substantially the same Raman spectrum of FIG. 12.

16. Pterostilbene Form II of claim 8, further having one or more x-ray powder diffraction peaks at about 12.6 or 15.7°2θ.

17. Pterostilbene Form II of claim 8, having substantially the same x-ray powder diffraction pattern of FIG. 3 when measured with Cu—K$_\alpha$ radiation.

18. Pterostilbene Form II of claim 8, having substantially the same Raman spectrum of FIG. 13.

19. Pterostilbene Form III of claim 9, having substantially the same x-ray powder diffraction pattern of FIG. 5 when measured with Cu—K$_\alpha$ radiation.

20. Pterostilbene Form III of claim 9, having substantially the same Raman spectrum as FIG. 14.

21. Pterostilbene Form IV of claim 10, having substantially the same x-ray powder diffraction pattern of FIG. 6 when measured with when measured with Cu—K$_\alpha$ radiation.

22. Pterostilbene Form IV of claim 10, having substantially the same Raman spectrum of FIG. 15.

23. Pterostilbene Form V of claim 11, having substantially the same x-ray powder diffraction pattern of FIG. 7 when measured with Cu—K$_\alpha$ radiation.

24. Pterostilbene Form V of claim 11, having substantially the same Raman spectrum of FIG. 16.

25. A t-butanol solvate of Pterostilbene having substantially the same x-ray powder diffraction pattern as FIG. 8.

26. Pterostilbene Form I of claim 7, having Raman peaks at about 195, 865, and 1358 cm$^{-1}$.

27. Pterostilbene Form I of claim 7, having Raman peaks at about 865 and 1358 cm$^{-1}$.

28. Pterostilbene Form II of claim 8, having Raman peaks at about 960, 1442, and 1587 cm$^{-1}$.

29. Pterostilbene Form III of claim 9, having Raman peaks at about 958, 1187, and 1439 cm$^{-1}$.

30. Pterostilbene Form IV of claim 10, having Raman peaks at about 862 cm$^{-1}$ and 1320 cm$^{-1}$ and a melting point of about 76° C.

31. Pterostilbene Form IV of claim 10, having Raman peaks at about 200, 862, and 1320 cm$^{-1}$.

32. Pterostilbene Form IV of claim 31, further having a melting point of about 76° C.

33. Pterostilbene Form V of claim 11, having Raman peaks at about 867, 962, and 1444 cm$^{-1}$.

34. A process for preparing the Pterostilbene Form I of claim 7, comprising the steps of:
    treating a solution of (2-4-[(E)-2-(3,5-dimethoxyphenyl)-1-ethenyl]phenoxy tetra hydro-2H-pyran) with pyridinium p-toluenesulfonate in methanol;
    removing the methanol to obtain a solid;
    dissolving the solid in ethyl acetate; and
    precipitating Pterostilbene Form I with acetone.

35. A process for preparing the Pterostilbene Form II of claim 8, comprising the steps of:
    dissolving a Pterostilbene Form I in trifluoroethanol, wherein the Pterostilbene Form I has x-ray powder diffraction peaks, when measured with Cu—Kα radiation, at about 16.7 and 8.3°2θ, and a melting point of about 94-96° C.; and
    cooling to precipitate Pterostilbene Form II.

36. A process for preparing the Pterostilbene Form II of claim 8, comprising the steps of:
    dissolving solid Pterostilbene in acetonitrile; and
    evaporating the acetonitrile to precipitate Pterostilbene Form II.

37. A process for preparing the Pterostilbene Form III of claim 9, comprising the steps of
    dissolving solid Pterostilbene in methanol; and
    evaporating the methanol to precipitate Pterostilbene Form III.

38. A process for preparing the Pterostilbene Form IV of claim 10, comprising the steps of:
    dissolving solid Pterostilbene in methanol; and
    slowly evaporating the methanol to precipitate Pterostilbene Form IV.

39. A process for preparing the Pterostilbene Form V of claim 11, comprising the steps of exposing amorphous Pterostilbene at less than 10% relative humidity and room temperature to form Pterostilbene Form V.

* * * * *